US012673035B2

(12) United States Patent
Roudot et al.

(10) Patent No.: US 12,673,035 B2
(45) Date of Patent: Jul. 7, 2026

(54) SOLID DOSAGE FORMS OF ELAFIBRANOR

(71) Applicant: Genfit, Loos (FR)

(72) Inventors: Alice Roudot, Lomme (FR);
Marie-Jeanne Joissains, Plomelin (FR)

(73) Assignee: Genfit, Loos (FR)

( * ) Notice: Subject to any disclaimer, the term of this patent is extended or adjusted under 35 U.S.C. 154(b) by 0 days.

(21) Appl. No.: 19/302,463

(22) Filed: Aug. 18, 2025

(65) Prior Publication Data

US 2026/0027075 A1    Jan. 29, 2026

Related U.S. Application Data

(63) Continuation of application No. PCT/EP2024/055754, filed on Mar. 5, 2024.

(30) Foreign Application Priority Data

Mar. 6, 2023    (EP) ..................................... 23305292

(51) Int. Cl.
| | |
|---|---|
| *A61K 31/192* | (2006.01) |
| *A61K 9/20* | (2006.01) |
| *A61K 9/28* | (2006.01) |
| *A61P 1/16* | (2006.01) |

(52) U.S. Cl.
CPC .......... *A61K 31/192* (2013.01); *A61K 9/2009* (2013.01); *A61K 9/2013* (2013.01); *A61K 9/2027* (2013.01); *A61K 9/2054* (2013.01); *A61K 9/2095* (2013.01); *A61K 9/2806* (2013.01); *A61P 1/16* (2018.01)

(58) Field of Classification Search
CPC .. A61K 31/192; A61K 9/2009; A61K 9/2013; A61K 9/2027; A61K 9/2054; A61K 9/2095; A61K 9/2806; A61P 1/16
See application file for complete search history.

(56) References Cited

U.S. PATENT DOCUMENTS 11,185,520 B2    11/2021    Laruelle et al.
2019/0274982 A1 *    9/2019    Laruelle ............... A61K 9/0019

FOREIGN PATENT DOCUMENTS

| WO | WO-2020208594 A1 * | 10/2020 | .......... A61K 31/192 |
|---|---|---|---|
| WO | 2021/160519 A1 | 8/2021 | |
| WO | 2022/051323 A1 | 3/2022 | |

OTHER PUBLICATIONS

International Search Report prepared for PCT application No. PCT/EP2024/055754, dated May 16, 2024.

* cited by examiner

*Primary Examiner* — Quanglong N Truong
(74) *Attorney, Agent, or Firm* — Morse, Barnes-Brown & Pendleton, P.C.; Erin E. Bryan, Esq.; Russell L. Widom

(57) ABSTRACT

The present invention relates to formulations of elafibranor or a pharmaceutically acceptable salt or ester thereof; and uses thereof. In particular, the present invention relates to an oral solid dosage form comprising at least elafibranor or a pharmaceutically acceptable salt or ester thereof; a filler, a disintegrating agent and a binder.

15 Claims, 10 Drawing Sheets

| Tests on 80 mg tablets (Formulation 1) | specifications | T0 | 1 month | 2 months | 3 months | 6 months | 9 months | 12 months | 24 months | 36 months |
|---|---|---|---|---|---|---|---|---|---|---|
| Tablet Appearance | White round tablet | OK | OK | OK | OK | OK | OK | OK | OK | OK |
| Mean mass (mg) | 220.0 mg (± 5.0%) | 220.3 | 222.5 | 222.2 | 222.7 | 220.8 | 222.7 | 222.0 | 223.3 | 223.0 |
| Mass uniformity | Complies | OK | OK | OK | OK | OK | OK | OK | OK | OK |
| Disintegration time (min) | ≤ 15 min | 3 | 3 | 2 | 2 | 2 | 3 | 2 | 6 | 2 |
| Dissolution rate (%) | At 15 min | 93 | | | 95 | 97 | 95 | 94 | 91 | 94 |

FIG. 1

| Tests on 120 mg tablets (Formulation 2) | specifications | T0 | 3 months | 6 months | 12 months | 18 months | 24 months | 36 months |
|---|---|---|---|---|---|---|---|---|
| Tablet Appearance | White round tablet | OK | OK | OK | OK | OK | OK | OK |
| Mean mass (mg) | 328.0 mg (± 5.0%) | 332.2 | 330.7 | 328.7 | 329.3 | 329.0 | 329.6 | 331.5 |
| Mass uniformity | Complies | OK | OK | OK | OK | OK | OK | OK |
| Disintegration time (min) | ≤ 15 min | 4 | 3 | 4 | 4 | 3 | 4 | 5 |
| Dissolution rate (%) | At 15 min | 86 | 91 | 90 | 90 | 89 | 89 | 87 |

FIG. 2

| Tests on 80mg tablets (Formulation 4) | Specifications | T0 | 3 months | 6 months | 9 months | 12 months | 18 months |
|---|---|---|---|---|---|---|---|
| Tablet Appearance | White round tablet | OK | OK | OK | OK | OK | OK |
| Mean mass (mg) | 209.3 (± 7.50%) | 209.8 | 210.0 | 210.1 | 209.7 | 209.5 | 209.6 |
| Mass uniformity | Complies | OK | OK | OK | OK | OK | OK |
| Active ingredient content (HPLC) | 80.0mg (±5%) | 78.8 | 78.6 | 79.1 | 78.5 | 78.1 | 78.3 |
| Disintegration time (min) | ≤ 15 min | 4 | 3 | 4 | 3 | 4 | 3 |
| Dissolution rate (%) | At 30 mn | 96 | 94 | 96 | | 93 | |

| | Specifications | | 24 months | 30 months | 36 months | 48 months | 60 months |
|---|---|---|---|---|---|---|---|
| Tablet Appearance | White round tablet | | OK | OK | OK | OK | OK |
| Mean mass (mg) | 209.3mg (± 7.50%) | | 209.5 | 208.6 | 210.7 | 209.4 | 209.9 |
| Mass uniformity | Complies | | OK | OK | OK | OK | OK |
| Active ingredient content (HPLC) | 80.0mg (±5%) | | 78.7 | 79.7 | 78.4 | 78.1 | 78.6 |
| Disintegration time (min) | ≤ 15 min | | 3 | 3 | 3 | 4 | 3 |
| Dissolution rate (%) | At 30 min | | 95 | 93 | 91 | 94 | 95 |

FIG. 3

| Tests on 120mg tablets (Formulation 3) | specifications | T0 | 3 months | 6 months | 9 months | 12 months |
|---|---|---|---|---|---|---|
| Tablet Appearance | White round tablet | OK | OK | OK | OK | OK |
| Mean mass (mg) | 314.0 mg (± 5.0%) | 316.0 | 315.6 | 316.2 | 315.9 | 317.0 |
| Mass uniformity | Complies | OK | OK | OK | OK | OK |
| Active ingredient content (HPLC) | 120.0mg (±5%) | 119.5 | 119.4 | 119.7 | 118.9 | 120.7 |
| Disintegration time (min) | ≤ 15 min | 5 | 5 | 4 | 4 | 5 |
| Dissolution rate (%) | At 30 mn | | | 95 | | 96 |

| | | | 18 months | 24 months | 36 months | 48 months |
|---|---|---|---|---|---|---|
| Tablet Appearance | White round tablet | | OK | OK | OK | OK |
| Mean mass (mg) | 314.0 mg (± 5.0%) | | 315.9 | 315.4 | 316.7 | 317.3 |
| Mass uniformity | Complies | | OK | OK | OK | OK |
| Active ingredient content (HPLC) | 120.0mg (±5%) | | 118.9 | 117.8 | 120.0 | 120.0 |
| Disintegration time (min) | ≤ 15 min | | 4 | 3 | 5 | 5 |
| Dissolution rate (%) | At 30 min | | | 95 | 94 | 95 |

FIG. 4

| Statistic | | Elafibranor 80 mg N = 15 | Elafibranor 120 mg N = 14 | Placebo N = 15 |
|---|---|---|---|---|
| 10% Reduction in ALP levels | | | | |
| Response rate from Baseline to Endpoint (Visit 5 or EOT), n (%) | Responder | 14 (93.3) | 13 (92.9) | 2 (13.3) |
| | Non-responder | 1 (6.7) | 1 (7.1) | 13 (86.7) |
| | Fishers exact p-value | < 0.001 | < 0.001 | - |
| Elafibranor vs placebo | | | | |
| 20% Reduction in ALP levels | | | | |
| Response rate from Baseline to Endpoint (Visit 5 or EOT), n (%) | Responder | 14 (93.3) | 13 (92.9) | 1 (6.7) |
| | Non-responder | 1 (6.7) | 1 (7.1) | 14 (93.3) |
| | Fishers exact p-value | < 0.001 | < 0.001 | - |
| Elafibranor vs placebo | | | | |
| 40% Reduction in ALP levels | | | | |
| Response rate from Baseline to Endpoint (Visit 5 or EOT), n (%) | Responder | 13 (86.7) | 8 (57.1) | 0 |
| | Non-responder | 2 (13.3) | 6 (42.9) | 15 (100) |
| | Fishers exact p-value | < 0.001 | < 0.001 | - |
| Elafibranor vs placebo | | | | |

FIG. 7

| GGT (U/L) | Statistic | Elafibranor 80 mg N = 15 | Elafibranor 120 mg N = 14 | Placebo N = 15 |
|---|---|---|---|---|
| Baseline | Mean ± SD | 282.3 ± 215.7 | 158.5 ± 144.6 | 229.6 ± 115.9 |
| | Median | 225.0 | 114.0 | 201.0 |
| Endpoint (Visit 5 or EOT value) | Mean ± SD | 190.8 ± 171.2 | 96.6 ± 90.8 | 230.2 ± 125.3 |
| | Median | 118.0 | 58.0 | 169.0 |
| | | | | |
| Absolute change from baseline to Endpoint | Mean ± SD | -91.5 ± 95.3 | -61.9 ± 70.8 | 0.6 ± 54.4 |
| | Median | -48.0 | -46.5 | -4.0 |
| Treatment effect (vs placebo)[a] | Estimate | -77.7 | -82 | |
| | 95% CI | [-123.4 ; -32.0] | [-128.8 ; -35.1] | - |
| | p-value | 0.001 | 0.001 | |
| Interaction: Baseline*trt | p-value | | 0.093 | |
| | | | | |
| Relative change from baseline to Endpoint (%) | Mean ± SD | -37.1 ± 25.5 | -40.0 ± 24.1 | 0.2 ± 26.0 |
| | Median | -41.0 | -40.7 | -2.8 |
| Treatment effect (vs placebo)[b] | Estimate | -38.6 | -39.9 | |
| | 95% CI | [-56.8 ; -20.4] | [-58.1 ; -21.6] | - |
| | p-value | 0.001 | 0.002 | |

FIG. 8

SOLID DOSAGE FORMS OF ELAFIBRANOR

RELATED APPLICATIONS

This application is a continuation of International Application No. PCT/EP2024/055754, filed Mar. 5, 2024, which claims the benefit of and priority to European Application No. 23305292.7, filed Mar. 6, 2023. The entire teachings of the above applications are incorporated herein by reference. International Application No. PCT/EP2024/055754 was published under PCT Article 21(2) in English.

FIELD OF THE INVENTION

The present invention relates to formulations of elafibranor and uses thereof.

BACKGROUND OF THE INVENTION

Elafibranor is a molecule that was first disclosed in WO2004005233. As a dual PPARα/δ agonist, elafibranor offers great promises in the treatment of different conditions. It was first described as useful in the treatment of a number of metabolic disorders and was since found efficient in treating cholestatic diseases, especially, in treating primary biliary cholangitis (PBC) during a phase 2 clinical trial. Elafibranor was evaluated in a phase 3 clinical trial for the treatment of PBC (ClinicalTrials.gov Identifier: NCT04526665). Treatment with elafibranor resulted in significantly greater improvements in relevant biochemical indicators of cholestasis than placebo (N Engl J Med. 2023 Nov. 13. doi: 10.1056/NEJMoa2306185). In view of these positive outcomes, Marketing Authorization Applications were recently validated by EMA (European Medicines Agency) and FDA (Food and Drug Administration). Consequently, elafibranor could potentially be the first novel second-line treatment for PBC, and would benefit from improved formulations.

SUMMARY OF THE INVENTION

The present invention relates to novel compositions of elafibranor or of a pharmaceutically acceptable salt or ester thereof.

In a first aspect, the present disclosure relates to an oral solid dosage form comprising a micronized form of elafibranor or of a pharmaceutically acceptable salt or ester of elafibranor. In a particular embodiment, said micronized form of elafibranor or of a pharmaceutically acceptable salt or ester thereof comprises at least 90% of particles having a diameter of 15 μm or less. In another particular embodiment, said micronized form of elafibranor or of a pharmaceutically acceptable salt or ester thereof comprises at least 50% of particles having a diameter of 5 μm or less. In yet another embodiment, said micronized form of elafibranor or of a pharmaceutically acceptable salt or ester thereof comprises:

at least 90% of particles having a diameter of 15 μm or less; and at least 50% of particles having a diameter of 5 μm or less.

In a second aspect, the present disclosure provides an oral solid dosage form comprising:

i) elafibranor or a pharmaceutically acceptable salt or ester thereof;

ii) a filler;

iii) a disintegrating agent; and iv) a binder.

In a particular embodiment, the oral solid dosage form comprises:

i) elafibranor or a pharmaceutically acceptable salt or ester thereof;

ii) a filler selected in the group consisting of mannitol, microcrystalline cellulose and lactose monohydrate;

iii) a disintegrating agent selected in the group consisting of crospovidone and croscarmellose sodium; and iv) a binder selected in the group consisting of hydroxypropylcellulose, copovidone, povidone and hydroxypropylmethylcellulose.

In a particular embodiment, elafibranor or a pharmaceutically acceptable salt or ester thereof is in a micronized form, such as the micronized form disclosed herein.

In a particular embodiment, the filler is microcrystalline cellulose.

In a particular embodiment, the disintegrating agent is croscarmellose sodium.

In a particular embodiment, the binder is povidone.

In a particular embodiment, the oral dosage form comprises:

i) elafibranor or a pharmaceutically acceptable salt or ester thereof;

ii) microcrystalline cellulose;

iii) croscarmellose sodium; and iv) povidone.

In yet another particular embodiment, the oral dosage form comprises:

i) a micronized form of elafibranor or of a pharmaceutically acceptable salt or ester thereof;

ii) microcrystalline cellulose;

iii) croscarmellose sodium; and iv) povidone.

In a further particular embodiment, the oral solid dosage form is a tablet. In yet another particular embodiment, the tablet comprises:

(a) an internal phase which comprises:

(i) elafibranor or a pharmaceutically acceptable salt or ester thereof;

(ii) a filler;

(iii) a disintegrating agent; and (iv) a binder; and (b) an external phase comprising a disintegrating agent, a glidant and a lubricant.

In a particular embodiment, the oral solid dosage form comprises as lubricant, magnesium stearate.

In another particular embodiment, the oral solid dosage form comprises as glidant, an anhydrous colloidal silica.

In another particular embodiment, the oral solid dosage form is a coated tablet.

In a particular embodiment, the tablet comprises a granulate as an internal phase.

In a particular embodiment, the internal phase of the tablet comprises:

(i) elafibranor or a pharmaceutically acceptable salt or ester thereof;

(ii) microcrystalline cellulose;

(iii) croscarmellose sodium; and (iv) povidone.

In yet another particular embodiment, the internal phase of the tablet comprises:

(i) a micronized form of elafibranor or of a pharmaceutically acceptable salt or ester thereof;

(ii) microcrystalline cellulose;

(iii) croscarmellose sodium; and (iv) povidone.

In another particular embodiment, the dosage form according to the invention comprises at least 20% of elafibranor, preferably at least 35% of elafibranor. In a further particular embodiment, the dosage form comprises from 20 to 60% by weight of elafibranor or of a pharmaceutically acceptable salt or ester thereof. In a further embodiment, the dosage form comprises from 35 to 40% by weight of elafibranor or of a pharmaceutically acceptable salt or ester thereof. In a further embodiment, the dosage form comprises from 35 mg to 180 mg (preferably from 40 mg to 120 mg) of elafibranor or of a pharmaceutically acceptable salt or ester thereof.

In a further embodiment, the dosage form comprises 40 mg of elafibranor or of a pharmaceutically acceptable salt or ester thereof. In another particular embodiment, the dosage form comprises 80 mg of elafibranor or of a pharmaceutically acceptable salt or ester thereof. In a further particular embodiment, the dosage form comprises 120 mg of elafibranor or of a pharmaceutically acceptable salt or ester thereof. In another particular embodiment, the dosage form comprises 180 mg of elafibranor or of a pharmaceutically acceptable salt or ester thereof.

According to a particular embodiment, at least 75% of elafibranor, or of a pharmaceutically acceptable salt or ester thereof, is released within 15 minutes from the oral solid dosage form, when tested according to the European Pharmacopeia 5.0, paragraph 2.9.3 with a paddle apparatus at 75 rpm, 37° C.±0.5° C. and 1000 mL of SDS in water, respectively 0.6% SDS for 40 mg dosage, 0.8% SDS for 80 mg dosage and 1% SDS for 120 mg dosage.

According to another particular embodiment, at least 90% of elafibranor, or a pharmaceutically acceptable salt or ester thereof, is released within 30 minutes, from the oral solid dosage form, when tested according to the European Pharmacopeia 5.0, paragraph 2.9.3 with a paddle apparatus at 75 rpm, 37° C.±0.5° C. and 1000 mL of SDS in water, respectively 0.6% SDS for 40 mg dosage, 0.8% SDS for 80 mg dosage and 1% SDS for 120 mg dosage.

The present disclosure also relates to the dosage forms disclosed herein for use in a method for treating a disease in a subject that would benefit from the activation of PPAR (peroxisome proliferator-activated receptor).

The present disclosure further relates to a method for treating a disease in a subject that would benefit from the activation of PPAR (peroxisome proliferator-activated receptor), by administering an oral solid dosage form as disclosed herein to the subject in need thereof.

The present disclosure further relates to the use of the dosage forms disclosed herein for the manufacture of a medicament for the treatment of a disease in a subject that would benefit from the activation of PPAR (peroxisome proliferator-activated receptor).

In a particular embodiment, the disease is selected in the group consisting of PBC, PSC (primary sclerosing cholangitis), NAFLD (non-alcoholic fatty liver disease), NASH (non-alcoholic steatohepatitis), hepatitis C infection, alcoholic liver disease, liver damage due to progressive fibrosis, liver fibrosis and cirrhosis. In a preferred instance, the disease is PBC or PSC, more preferably PBC.

Another aspect of the disclosure relates to a method of treating PBC in a patient in need thereof by administering an oral solid dosage form as disclosed herein, wherein the dosage form is a dosage unit, wherein the dosage unit, preferably a tablet, contains at least 35% of elafibranor, and wherein at least 75% of the dosage unit is dissolved in less than 15 minutes, when tested according to the European Pharmacopeia 5.0, paragraph 2.9.3 with a paddle apparatus at 75 rpm, 37° C.±0.5° C. and 1000 mL of SDS in water, respectively 0.6% SDS for 40 mg dosage, 0.8% SDS for 80 mg dosage and 1% SDS for 120 mg dosage.

The disclosure further relates to the oral solid dosage form as disclosed herein, for use in a method for treating PBC, wherein the dosage form is a dosage unit, wherein the dosage unit, preferably a tablet, contains at least 35% of elafibranor, and wherein at least 75% of the dosage unit is dissolved in less than 15 minutes, when tested according to the European Pharmacopeia 5.0, paragraph 2.9.3 with a paddle apparatus at 75 rpm, 37° C.±0.5° C. and 1000 mL of SDS in water, respectively 0.6% SDS for 40 mg dosage, 0.8% SDS for 80 mg dosage and 1% SDS for 120 mg dosage.

The disclosure further relates to the use the oral solid dosage form as disclosed herein, in the manufacture of a medicament for the treatment of PBC, wherein the dosage form is a dosage unit, wherein the dosage unit, preferably a tablet, contains at least 35% of elafibranor, and wherein at least 75% of the dosage unit is dissolved in less than 15 minutes, when tested according to the European Pharmacopeia 5.0, paragraph 2.9.3 with a paddle apparatus at 75 rpm, 37° C.±0.5° C. and 1000 mL of SDS in water, respectively 0.6% SDS for 40 mg dosage, 0.8% SDS for 80 mg dosage and 1% SDS for 120 mg dosage.

In still another aspect of the disclosure is a method of treating cholestatic or hepatic conditions like PBC, PSC, NAFLD, NASH, cirrhosis, hepatitis C infection, alcoholic liver disease, liver damage due to progressive fibrosis, or liver fibrosis in a patient in need thereof by administering a composition that includes elafibranor, or a pharmaceutically acceptable salt or ester thereof, wherein elafibranor or a pharmaceutically acceptable salt or ester thereof is in the form of particles. In one embodiment, 90% of the particles have a diameter of 15 μm or less. In a further embodiment, 50% of the particles have a diameter of 5 μm or less. In yet another embodiment, 90% of the particles have a diameter of 15 μm or less and 50% of the particles have a diameter of 5 μm or less.

The disclosure further relates to a composition that includes elafibranor, or a pharmaceutically acceptable salt or ester thereof, for use in a method of treating cholestatic or hepatic conditions like PBC, PSC, NAFLD, NASH, cirrhosis, hepatitis C infection, alcoholic liver disease, liver damage due to progressive fibrosis, or liver fibrosis, wherein elafibranor or a pharmaceutically acceptable salt or ester thereof is in the form of particles. In one embodiment, 90% of the particles have a diameter of 15 μm or less. In a further embodiment, 50% of the particles have a diameter of 5 μm or less. In yet another embodiment, 90% of the particles have a diameter of 15 μm or less and 50% of the particles have a diameter of 5 μm or less.

The disclosure further relates to the use of a composition that includes elafibranor, or a pharmaceutically acceptable salt or ester thereof, for the manufacture of a medicament for the treatment of cholestatic or hepatic conditions like PBC, PSC, NAFLD, NASH, cirrhosis, hepatitis C infection, alcoholic liver disease, liver damage due to progressive fibrosis, or liver fibrosis, wherein elafibranor or a pharmaceutically acceptable salt or ester thereof is in the form of particles. In one embodiment, 90% of the particles have a diameter of 15 μm or less. In a further embodiment, 50% of the particles have a diameter of 5 μm or less. In yet another embodiment, 90% of the particles have a diameter of 15 μm or less and 50% of the particles have a diameter of 5 μm or less.

BRIEF DESCRIPTION OF THE FIGURES

FIG. 1 is a table showing the dissolution release rate and the stability of tablets of Formulation 1 containing 80 mg of jet-milled elafibranor.

FIG. 2 is a table showing the dissolution release rate and the stability of tablets of Formulation 2 containing 120 mg of jet-milled elafibranor.

FIG. 3 is a table showing the dissolution release rate and the stability of tablets containing 80 mg of Formulation 4 of jet-milled elafibranor.

FIG. 4 is a table showing the dissolution release rate and the stability of tablets containing 120 mg of Formulation 3 of jet-milled elafibranor.

FIG. 7 is a table showing the reduction of ALP levels analyzed using a Fishers exact test on the modified intent-to-treat (mITT) set, in subjects treated with an oral solid dosage form according to the invention containing either 80 mg or 120 mg of elafibranor (Formulations 4 and 3). Abbreviations: ALP: alkaline phosphatase; EOT=end-of-treatment.

FIG. 8 is a table showing the absolute and relative change from baseline in γ-glutamyl transpeptidase (mITT Set). Abbreviations: CI=confidence interval; EOT=end-of-treatment; GGT=γ-glutamyl transpeptidase; SD=standard deviation.

DETAILED DESCRIPTION OF THE INVENTION

Figure 5:
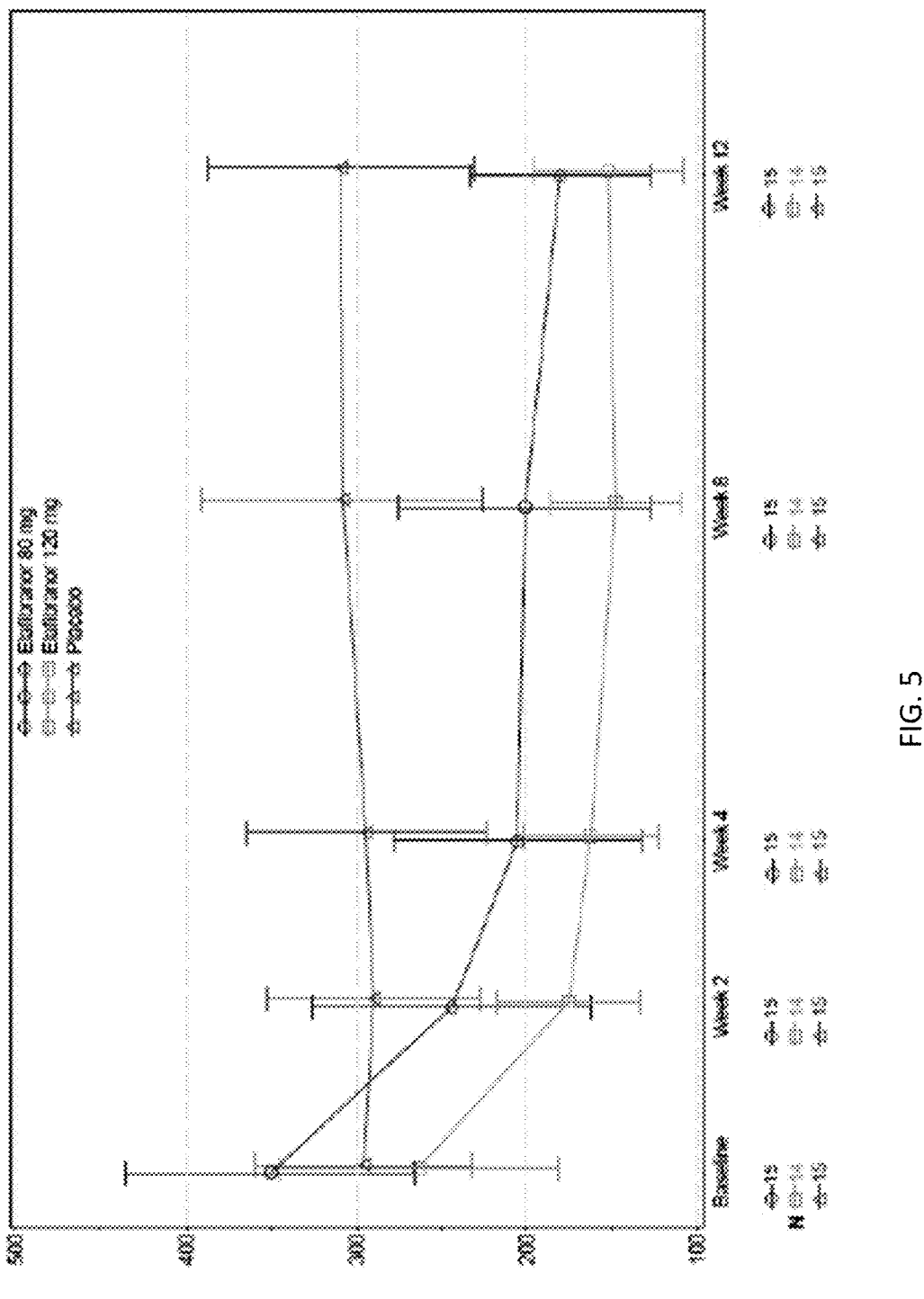
FIG. 5 is a graph showing the absolute change from baseline through week 12 in alkaline phosphatase (ALP) in groups of patients treated with an oral solid dosage form according to the invention, comprising either 80 mg or 120 mg of elafibranor (Formulations 4 and 3).

Usually, powders are tableted by direct compression or granules are produced and tableted. However, tableting by direct compression and granulation are largely affected by the physical properties of the drug and often have great weight variations and poor content uniformity at the time of tableting, resulting in poor manufacturability in consideration of productivity. Moreover, these approaches can provide a drug product with poor dissolution. The present disclosure provides oral dosage forms of elafibranor or pharmaceutically acceptable salts or esters thereof that that do not have these issues.

Unless defined otherwise, all technical and scientific terms used herein have the same meaning as commonly understood by one of ordinary skill in the art to which this disclosure belongs.

All percentages and ratios used herein, unless otherwise indicated, are by weight.

The term "filler" as used herein, refers to an agent that adds bulk to very small active ingredients. Examples of fillers include mannitol, microcrystalline cellulose, lactose (e.g. lactose monohydrate), and mixtures thereof.

The term "binder" as used herein refers to an agent or a mixture of agents that increases the thickness of a liquid thereby keeping the active ingredient suspended to allow accurate dosing. Binders include, but are not limited to, povidone, copovidone, hydroxypropyl cellulose, hydroxypropyl methylcellulose and mixtures thereof.

The term "disintegrating agent" as used herein refers to an agent that aids in the disintegration of an oral solid dosage form. Illustrative disintegrating agents include crospovidone, croscarmellose sodium, and mixtures thereof.

The term "glidant" as used herein refers to an agent that is added to a powder to improve its flowability. Illustrative glidants include silica, preferably colloidal silica, more preferably anhydrous colloidal silica.

The term "lubricant" as used herein refers to a substance that helps to reduce friction between surfaces in mutual contact. Illustrative lubricants include magnesium stearate, calcium stearate, stearic acid, glyceryl behenate, hydrogenated vegetable oil, and glycerine fumarate, and/or combinations thereof. In a particular embodiment, the lubricant is magnesium stearate.

The term "organ" refers to a differentiated structure (as in a heart, lung, kidney, liver, etc.) consisting of cells and tissues and performing some specific function in an organism. This term also encompasses bodily parts performing a function or cooperating in an activity (e.g., an eye and related structures that make up the visual organs). The term "organ" further encompasses any partial structure of differentiated cells and tissues that is potentially capable of developing into a complete structure (e.g., a lobe or a section of a liver).

"Elafibranor" refers to 2-[2,6-dimethyl-4-[(E)-3-(4-methylsulfanylphenyl)-3-oxoprop-1-enyl]phenoxy]-2-methylpropanoic acid, a compound formerly called GFT505. In the context of the present disclosure, the term "elafibranor" refers to all forms of elafibranor, e.g. non-crystalline, crystalline and substantially pure.

Any reference to a dose, amount or percentage of elafibranor in this disclosure is based on the free base equivalent weight of elafibranor. For example, 35 mg of elafibranor refers to 35 mg of elafibranor in the free base form or an equivalent amount of a salt or ester of elafibranor.

An "elafibranor composition" or "pharmaceutical composition" described herein refers to an oral solid dosage form according to the invention, i.e. comprising elafibranor or a pharmaceutically acceptable salt or ester thereof, in particular elafibranor or a pharmaceutically acceptable salt thereof, more specifically an oral solid dosage form comprising elafibranor.

The articles "a" and "an" are used in this disclosure to refer to one or more than one (i.e. to at least one) of the grammatical object of the article. By way of example, "an element" means one element or more than one element.

The term "and/or" is used in this disclosure to mean either "and" or "or" unless indicated otherwise.

As used herein, the term "purity" refers to a chemical analysis of a compound obtained from, e.g., HPLC. The purity of elafibranor may be calculated via the surface area of the peak. In one embodiment, purity accounts for the organic impurities in a sample. In one embodiment, the purity of elafibranor is at least of 98% of the surface area of the peak, preferably at least 99%.

"Treating", includes any effect, e.g., lessening, reducing, modulating, or eliminating, that results in the improvement of the condition, disease or disorder.

"Treating" or "treatment" of a disease state includes: inhibiting the disease state, i.e., arresting the development of the disease state or its clinical symptoms; or relieving the disease state, i.e. causing temporary or permanent regression of the disease state or its clinical symptoms.

The term "regimen" refers to a protocol for dosing and/or timing the administration of one or more therapies (e.g., an elafibranor oral solid dosage form described herein or another active agent such as for example UDCA) for treating a disease, disorder, or condition described herein. A regimen can include periods of active administration and periods of rest as known in the art. Active administration periods include administration of the oral solid dosage form described herein in a defined course of time, including, for example, the number of and timing of dosages of the compositions. In some regimens, one or more rest periods can be included where no compound is actively administered.

"Preventing" the disease state includes causing the clinical symptoms of the disease state not to develop in a subject that may be exposed to or predisposed to the disease state but does not yet experience or display symptoms of the disease state.

As used herein, the term "inhibiting" or "inhibition", as applied to a disease or condition, refers to any detectable positive effect on the development or progression of a disease or condition. Such a positive effect may include the delay or prevention of the onset of at least one symptom or sign of the disease or condition, alleviation or reversal of the symptom(s) or sign(s) and slowing or prevention of the further worsening of the symptom(s) or sign(s).

"Disease state" means any disease, disorder, condition, symptom, or indication.

The term "effective amount" as used herein refers to an amount of elafibranor, or of a pharmaceutically acceptable salt or ester thereof, that produces an acute or chronic therapeutic effect upon appropriate dose administration. The effect includes the prevention, correction, inhibition, or reversal of the symptoms, signs and underlying pathology of a disease/condition and related complications to any detectable extent.

For any compound, the therapeutically effective amount can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity are determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred.

The toxicology program performed according to the International Council for Harmonisation (ICH) guidelines demonstrates that elafibranor has no genotoxic or mutagenicity potential. According to acute toxicity study results, it can be concluded that elafibranor is extremely safe when administered as single oral doses in rat and mouse, since no sign of toxicity was detected up to the dose of 1000 mg/kg.

Dosage and administration are adjusted to provide sufficient levels of the active agent(s) or to maintain the desired effect. Factors taken into account include the severity of the disease state, general health of the subject, age, weight, and gender of the subject, diet, time and frequency of administration, drug combination(s), reaction sensitivities, and tolerance/response to therapy.

The term "administering" refers to the act of delivering an oral solid dosage form described herein into a subject by oral administration. The term can also refer to the frequency (e.g., daily, weekly, monthly, etc.) of providing the oral solid dosage form described herein to a patient. Administration generally occurs after the onset of the disease, disorder, or condition, or its symptoms but, in certain instances, can occur before the onset of the disease, disorder, or condition, or its symptoms (e.g., administration for patients prone to such a disease, disorder, or condition).

An oral solid dosage form of the instant invention can be administered alone or can be coadministered to the patient. Co-administration is meant to include simultaneous or sequential administration of the oral solid dosage form individually or in combination (more than one compound or agent). Thus, the oral solid dosage form can also be combined, when desired, with other active substances. Such other active substances include substances useful to reduce metabolic degradation of elafibranor or a pharmaceutically acceptable salt or ester thereof, and other active agents known to be useful in treating a disease such as UDCA (Ursodeoxycholic acid) or obeticholic acid. Alternatively, the oral solid dosage forms described herein can be used in combination with adjunctive agents that are not effective alone, but can contribute to or enhance the efficacy of the active agent.

The timing of co-administration depends in part of the combination and the compositions administered and can include administration at the same time, prior to, or after the administration of one or more additional therapies.

"Pharmacological effect" as used herein encompasses effects produced in the subject that achieve the intended purpose of a therapy. In one embodiment, a pharmacological effect means that primary indications of the subject being treated are prevented, alleviated, or reduced. For example, a pharmacological effect would be one that results in the prevention, alleviation or reduction of primary indications in a treated subject. In another embodiment, a pharmacological effect means that disorders or symptoms of the primary indications of the subject being treated are prevented, alleviated, or reduced. For example, a pharmacological effect would be one that results in the prevention or reduction of primary indications in a treated subject.

"Dosage unit form", or "dosage unit", as used herein, refers to physically discrete units suited as unitary dosages for the subject to be treated; each unit containing a predetermined quantity of active reagent calculated to produce the desired therapeutic effect. The specifications for the dosage unit forms of the disclosure are dictated by and directly dependent on the unique characteristics of the active reagent and the particular therapeutic effect to be achieved, and the limitations inherent in the art of compounding such an active agent for the treatment of individuals.

The unit dosage form is any of a variety of forms, including, for example, a capsule or a tablet. The quantity of elafibranor (e.g. elafibranor, or a pharmaceutically acceptable salt or ester thereof) in a dosage unit form is an effective amount and is varied according to the particular treatment involved. One skilled in the art will appreciate that it is sometimes necessary to make routine variations to the dosage, depending on the age and condition of the patient.

The term "immediate release" is defined as a release of elafibranor from a dosage form in a relatively brief period of time, generally up to about 30 minutes, in particular up to about 15 minutes.

A "subject" or "patient" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject or patient is human. Patients described herein include patients having a disease or condition described herein. A patient can be described or referred to by the condition treated. For example, a patient having PBC can be referred to herein as a PBC patient. A patient described herein can have a preexisting condition (e.g., a condition other than the disease or condition treated by the oral dosage form described herein that existed at the time of first administration). In one instance, the patient is an elderly/geriatric patient or a pregnant patient. In another instance the patient is a pediatric patient.

As used herein, the phrase "pharmaceutically acceptable" refers to those compounds, materials, compositions, fillers, binders, glidants, disintegrating agents and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration, i.e. oral route in the present disclosure.

A "control" as used herein refers to a baseline level determined on a patient-by-patient basis, an amount or level considered by those skilled in the art as a normal value, or any level or measure of a condition or biomarker described herein taken from a patient or population of patients at any given time for a given condition.

As used herein, a "cholestatic condition" or "cholestatic disease" refers to any disease or condition in which bile excretion from the liver is impaired or blocked, which can occur either in the liver or in the bile ducts. Intrahepatic cholestasis and extrahepatic cholestasis are the two types of cholestatic conditions. Intrahepatic cholestasis (which occurs inside the liver) is most commonly seen in primary biliary cholangitis, primary biliary cirrhosis, primary sclerosing cholangitis, sepsis (generalized infection), acute alcoholic hepatitis, drug toxicity and malignancy. Extrahepatic cholestasis (which occurs outside the liver) can be caused by bile duct tumors, strictures, cysts, diverticula, stone formation in the common bile duct, pancreatitis, pancreatic tumor or pseudocyst, and compression due to a mass or tumor in a nearby organ. Clinical symptoms and signs of a cholestatic condition include: itching (pruritus), fatigue, jaundiced skin or eyes, inability to digest certain foods, nausea, vomiting, pale stools, dark urine, and right upper quadrant abdominal pain. A patient with a cholestatic condition can be diagnosed and followed clinically based on a set of standard clinical laboratory tests, including measurement of levels of alkaline phosphatase, γ-glutamyl transpeptidase (GGT), 5' nucleotidase, bilirubin, bile acids, and cholesterol in a patient's blood serum. Generally, a patient is diagnosed as having a cholestatic condition if serum levels of all three of the diagnostic markers alkaline phosphatase, GGT, and 5' nucleotidase, are considered abnormally elevated. The normal serum level of these markers may vary to some degree from laboratory to laboratory and from procedure to procedure, depending on the testing protocol. Thus, a physician will be able to determine, based on the specific laboratory and test procedure, what an abnormally elevated blood level is for each of the markers. For example, a patient suffering from a cholestatic condition generally has greater than about 125 IU/L alkaline phosphatase, greater than about 65 IU/L GGT, and greater than about 17 NIL 5' nucleotidase in the blood. Because of the variability in the level of serum markers, a cholestatic condition may be diagnosed on the basis of abnormal levels of these three markers in addition to at least one of the symptoms mentioned above, such as itching (pruritus).

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

In the present disclosure, a "particle size reduction" is carried out for the purpose of crushing solid particles by the application of mechanical force such as impact, shearing, or friction thereto to reduce the particle sizes, thereby facilitating the formation of a homogeneous mixed state and improving the dissolution rate and bioavailability of the drug owing to the increased surface area (which refers to as specific surface area, or "SSA") of the drug. Known particle size reduction methods include, but are not limited to: high-speed rotating impact mills (hammer mills and impact mills), which reduce particle size by means of the impact force of a high-speed rotating hammer or pin in a chamber; carrier mills (ball mills or vibration mills) which reduce particle size powder by means of impact force or friction force in a rotating cylinder in which the powder and magnetic balls are placed; and fluid energy mills (jet mills), which reduce particle size by jetting compressed air and raw material particles from a nozzle and colliding the particles accelerated by the jet of air with swirling particles in a chamber. In one embodiment, the particle size of elafibranor is reduced using a jet mill.

"Micronization," as defined herein, is a reduction of particle size of an active ingredient, elafibranor or a pharmaceutically acceptable salt or ester thereof in the present disclosure, to a diameter that is less than about 15 μm. In some examples, elafibranor has a particle size distribution with a D90 of not more than 15 μm and a D50 of not more than 5 μm.

The oral solid dosage form of the present disclosure comprising elafibranor or a pharmaceutically acceptable salt or ester thereof, in the form of particles, offers improved dissolution and solubility.

The pharmaceutical composition includes the entire active ingredient and if the pharmaceutical composition contains a capsule shell, carrier, excipient, diluent, disintegrating agent, lubricant, binder, the measurement is performed with those components.

The disclosure also relates to isotopically-labeled elafibranor, or pharmaceutically acceptable salts or esters thereof, which are identical to those recited in formulae of the disclosure and following, but for the fact that one or more atoms are replaced by an atom having an atomic mass or mass number different from the atomic mass or mass number most commonly found in nature. Examples of isotopes that can be incorporated into elafibranor, or pharmaceutically acceptable salts or esters thereof include isotopes of hydrogen, carbon, nitrogen, fluorine, such as $^3$H, $^{11}$C, $^{14}$C and $^{18}$F. Elafibranor, or pharmaceutically acceptable salts or esters thereof that contain the aforementioned isotopes and/or other isotopes of other atoms are within the scope of the present disclosure. Isotopically-labeled elafibranor, or pharmaceutically acceptable salts or esters thereof, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled elafibranor, or pharmaceutically acceptable salts or esters thereof can generally be prepared by carrying out the procedures disclosed in the Examples of the disclosure, by substituting a readily available isotopically labeled reagent for a non-isotopically labeled reagent. In one embodiment, elafibranor, or pharmaceutically acceptable salts or esters thereof are not isotopically labeled. In one embodiment, deuterated elafibranor is useful for bioanalytical assays. In another embodiment, elafibranor, or pharmaceutically acceptable salts or esters thereof are radiolabeled.

In one embodiment, the pharmaceutical composition may further comprise a coating agent such as sugar-based coating agent, water-soluble film coating agent, enteric coating agent and delayed release coating agent or a coating composition comprising any combination thereof. Such coating agent may be useful, for example, to protect elafibranor from light. In another embodiment, the coating agent can be any coating agent known in the art. Examples of coating agents include, but are not limited to, saccharose used alone or together with any of the agents such as talc, calcium carbonate, calcium phosphate, calcium sulphate, gelatine, gum arabic, polyvinylpyrrolidone and pullulan or any combination thereof, cellulose derivatives such as hydroxypropyl cellulose, hydroxypropyl methyl cellulose, hydroxyethyl cellulose, methyl hydroxyethyl cellulose and sodium carboxymethyl cellulose; synthetic polymers such as polyvinyl acetal diethyl amino acetate, aminoalkyl methacrylate copolymers and polyvinylpyrrolidone; polysaccharides such as pullulan; hydroxypropyl methyl cellulose phthalate; hydroxypropyl methyl cellulose acetate succinate; carboxymethyl ethyl cellulose; cellulose acetate phthalate; acrylic acid derivatives such as methacrylic acid copolymer L, methacrylic acid copolymer LD and methacrylic acid copolymer S; natural substances such as shellac; titanium dioxide; polyvinyl alcohol, polyethylene glycol; talc; lecithin; and/or combinations thereof. In one embodiment, the coating agent is selected from hydroxypropyl cellulose, hydroxypropyl methyl cellulose, hydroxyethyl cellulose, methyl hydroxyethyl cellulose, sodium carboxymethyl cellulose, polyvinyl acetal diethyl amino acetate, polyvinyl alcohol, polyethylene glycol, and lecithin, or a combination thereof. In particular, the coating agent is Opadry® II (e.g., Opadry® II green, white, yellow, orange, etc.).

In a specific embodiment, the pharmaceutical composition further comprises a coloring agent (also named dye). If appropriate, the coloring agent may be added in the coating.

Preferably, the coloring agent is not white. More preferably the coloring agent is yellow, orange, green or blue.

In particular, the pharmaceutical composition further comprises a coloring agent selected from the group consisting of synthetic food colorants and natural colorants. The coloring agent can be a synthetic food colorant including, for example, Brilliant Blue FCF (E133), Indigotine (E132), Fast Green FCF (E143), Erythrosine (E127), Allura Red AC (E129), Tartrazine (E102), and Sunset Yellow FCF (E110).

The coloring agent can be an aluminium lake. The term "aluminium lake" refers to a pigment formed by the reaction of aluminum hydroxide with the food colorant.

In a preferred embodiment of the invention, the coloring agent is Sunset Yellow FCF aluminium lake.

Preferably, the pharmaceutically composition comprising elafibranor, or a pharmaceutically acceptable salt or ester thereof, is in solid particle form.

The percentage of the active ingredient (i.e., elafibranor, or a pharmaceutically acceptable salt or ester thereof) and various excipients in the oral solid dosage form of the present disclosure may vary. For example, the oral solid dosage form may comprise from 35 mg to 180 mg by oral dosage form of active ingredient, such as from 40 mg to 120 mg. Furthermore, the oral solid dosage form may comprise from 20 to 55%, in particular from 40% to 49%, or from 43% to 48% by weight of microcrystalline cellulose as a filler. Furthermore, the composition may comprise from 2% to 6%, or from 4% to 5% by weight of povidone as binder. Furthermore, the composition may comprise from 1% to 10%, in particular from 3.5% to 6.5% by weight of croscarmellose sodium as a disintegrating agent. Furthermore, the composition may comprise from 0.01% to 0.2% by weight of colloidal silica as a glidant. Furthermore, the composition may comprise from 0.5% to 1.5% by weight of magnesium stearate as a lubricant.

In a preferred embodiment, the oral solid dosage form disclosed herein is a tablet comprising elafibranor or a pharmaceutically acceptable salt thereof.

In a particular embodiment, it is herein disclosed a tablet comprising:
  (a) an internal phase comprising:
    (i) elafibranor or a pharmaceutically acceptable salt or ester thereof,
    (ii) a filler;
    (iii) a disintegrating agent;
    (iv) a binder; and
  (b) an external phase comprising a disintegrating agent, a glidant and a lubricant.

In a particular embodiment, at least 90%, preferably of elafibranor, or of a pharmaceutically acceptable salt or ester thereof, is released within 30 minutes, from the tablet, when tested according to the European Pharmacopeia 5.0, paragraph 2.9.3 with a paddle apparatus at 75 rpm, 37° C.±0.5° C. and 1000 mL of SDS in water, respectively 0.6% SDS for 40 mg dosage, 0.8% SDS for 80 mg dosage and 1% SDS for 120 mg dosage.

In a particular embodiment, at least 75%, preferably 80% of elafibranor, or of a pharmaceutically acceptable salt or ester thereof, is released within 15 minutes, from the tablet, when tested according to the European Pharmacopeia 5.0, paragraph 2.9.3 with a paddle apparatus at 75 rpm, 37° C.±0.5° C. and 1000 mL of SDS in water, respectively 0.6% SDS for 40 mg dosage, 0.8% SDS for 80 mg dosage and 1% SDS for 120 mg dosage.

In yet another particular embodiment, the tablet disclosed herein comprises:

(a) an internal phase comprising:
  (i) elafibranor or a pharmaceutically acceptable salt or ester thereof,
  (ii) a filler selected in the group consisting of mannitol, microcrystalline cellulose and lactose;
  (iii) a disintegrating agent selected in the group consisting of crospovidone and croscarmellose sodium; and
  (iv) a binder selected in the group consisting of HPC, copovidone, povidone and hydroxypropylmethyl cellulose; and (b) an external phase comprising a disintegrating agent selected in the group consisting of crospovidone and croscarmellose sodium, colloidal silica as a glidant and magnesium stearate as a lubricant.

In a further embodiment, the tablet comprises:

(a) an internal phase comprising:
  (i) elafibranor or a pharmaceutically acceptable salt or ester thereof,
  (ii) microcrystalline cellulose;
  (iii) croscarmellose sodium; and
  (iv) povidone; and (b) an external phase comprising croscarmellose sodium, colloidal silica and magnesium stearate.

In another particular embodiment, the tablet as disclosed herein comprises:

(a) an internal phase comprising:
  (i) from 20% to 60% by weight of elafibranor or a pharmaceutically acceptable salt or ester thereof,
  (ii) from 20% to 55% by weight of microcrystalline cellulose;
  (iii) from 0.8% to 6% by weight of croscarmellose sodium; and
  (iv) from 2% to 6% by weight of povidone; and (b) an external phase comprising:
  from 0.2% to 4% by weight of croscarmellose sodium;
  from 0.1% to 0.4% by weight of colloidal silica; and
  from 0.1% to 2% by weight of magnesium stearate;
  relative to the total weight of the tablet.

In yet another particular embodiment, the tablet further comprises an external coating (also called film coating). In a further embodiment, the tablet comprises from 2% to 10% by weight of an external coating, relative to the total weight of the tablet. Useful coating agents are listed above. In a particular embodiment, the coating contains a polyvinyl alcohol such as Opadry® II. In a specific embodiment, the external coating comprises a coloring agent (also named dye). Preferably, the coloring agent is not white. More preferably the coloring agent is yellow, orange, green or blue. The coloring agent can be a synthetic food colorant including, for example, Brilliant Blue FCF (E133), Indigotine (E132), Fast Green FCF (E143), Erythrosine (E127), Allura Red AC (E129), Tartrazine (E102), and Sunset Yellow FCF (E110). The coloring agent can also be an aluminium lake. The term "aluminium lake" refers to a pigment formed by the reaction of aluminum hydroxide with the food colorant.

In a preferred embodiment of the invention, the external coating comprises a coloring agent which is Sunset Yellow FCF aluminium lake.

In a particular embodiment, the tablet of the present disclosure comprises a micronized form of elafibranor or of a pharmaceutically acceptable salt or ester thereof. In another embodiment, said micronized form of elafibranor, or of a pharmaceutically acceptable salt or ester thereof, comprises at least 90% of particles having a diameter of 15 μm or less, and/or at least 50% of particles having a diameter of 5 μm or less.

In a preferred embodiment, the tablet comprises elafibranor. In another embodiment, the tablet comprises from 35 mg to 180 mg of elafibranor, in particular from 40 mg to 120 mg of elafibranor. In a further particular embodiment, the tablet comprises 40 mg of elafibranor. In another particular embodiment, the tablet comprises 80 mg of elafibranor. In a further particular embodiment, the tablet comprises 120 mg of elafibranor. In a further particular embodiment, the tablet comprises 180 mg of elafibranor.

In one embodiment, the oral solid dosage form useful in the methods of treating described herein is a composition provided in Example 3.

In another aspect, the present disclosure provides a method for preparing an oral solid dosage form containing a therapeutically effective amount of elafibranor, or a pharmaceutically acceptable salt or ester thereof, in the form of particles, comprising i) micronizing elafibranor or an acceptable salt or ester thereof until at least 90% of the particles have a diameter of less than 15 μm and/or at least 50% of the particles have a diameter of less than 5 μm; and ii) combining the micronized particles with at least one pharmaceutically acceptable excipient. In one embodiment, micronizing is carried out using a jet-mill.

Tablets can be manufactured via a manufacturing process comprising wet granulation, preferably wet granulation by roller compaction, followed by tablet compression and optionally coating. In particular, tablets can be manufactured via a manufacturing process comprising wet granulation by roller compaction, followed by tablet compression and coating. The process steps used to manufacture tablets may include: pre-blending, wet granulation, final blending, compression and coating.

Briefly, the wet granulation may be carried out as follows: elafibranor or a pharmaceutically acceptable salt or ester thereof (such as a micronized form thereof), a filler, a binder and a disintegrating agent are weighed and mixed together, before adding a wetting solution. The wet granulate is then screened into an air-fluidized bed tank through a rotary screen. Residual moisture may be determined at this step, before the drying step. The wet granulate may be fluidized and dried with inlet air. Drying step may then be stopped when residual moisture of the dried granulate is less than 10%, preferably less than 5% by weight of the total granulate. The dried granulate may be directly screened and a residual moisture analysis may be optionally performed.

Disintegrating agent, glidant and lubricant may then be mixed together with dried and calibrated granulate as prepared above.

Using a rotary tablet press, the final blend may be compressed to form the tablet. The compression parameters can be adjusted to produce tablets of the desired weight, hardness, thickness, and friability. The tablet press speed and feeder speed can also be adjusted to help reduce tablet weight variation.

In one embodiment, the oral dosage form of the elafibranor composition includes a film coating that includes one or more excipients selected from polyvinyl alcohol (partly hydrolyzed), titanium dioxide, macrogol (polyethylene glycol 3350), talc, and iron oxide. The film coating preferably further comprises a coloring agent (also named dye). Preferably, the coloring agent is not white. More preferably the coloring agent is yellow, orange, green or blue. The coloring agent can be a synthetic food colorant including, for example, Brilliant Blue FCF (E133), Indigotine (E132), Fast Green FCF (E143), Erythrosine (E127), Allura Red AC (E129), Tartrazine (E102), and Sunset Yellow FCF (E110). The coloring agent can also be an aluminium lake. The term "aluminium lake" refers to a pigment formed by the reaction of aluminum hydroxide with the food colorant.

In a preferred embodiment of the invention, the film coating comprises a coloring agent which is Sunset Yellow FCF aluminium lake. In a preferred embodiment of the invention, the oral dosage form of the elafibranor composition includes a film coating that includes one or more excipients selected from polyvinyl alcohol (partly hydrolyzed), titanium dioxide, macrogol (polyethylene glycol 3350), talc, iron oxide, and Sunset Yellow FCF aluminium lake.

In one embodiment, for the film coating, water and a coating material (like Opadry® II white, Opadry® II green, Opadry® II yellow or Opadry® II Orange, preferably Opadry® II green, Opadry® II yellow or Opadry® II Orange) can be mixed. The core tablets can then be coated with this mixture and tested for mass uniformity and mean mass, thickness, dissolution, disintegration time and aspect.

In another aspect, the present disclosure provides an oral solid dosage form as disclosed herein, for use in the treatment or prevention of a disease or condition.

In another aspect the present disclosure provides a method for treating or preventing a disease or condition, comprising administering an effective amount of an oral solid dosage form of the present disclosure to a patient in need thereof.

In another aspect, the present disclosure provides the use of an oral solid dosage form as disclosed herein, for the manufacture of a medicament for the treatment or prevention of a disease or condition.

It will be understood that the amount of elafibranor actually administered will be determined by a physician, in the light of the relevant circumstances, including the condition to be treated, the chosen route of administration, the form of elafibranor administered, the age, weight, and response of the individual patient, and the severity of the patient's symptoms, and therefore the above dosage ranges are not intended to limit the scope of the disclosure in any way. In some instances, dosage levels below the lower limit of the aforesaid range may be more than adequate, while in other cases still larger doses may be employed without causing any harmful side effect. In an embodiment, these larger doses may be first divided into several smaller doses for administration throughout the day.

Examples of diseases or conditions include, but are not limited to cholestatic diseases, fibrosis and liver diseases. In particular, the disease or condition may selected from the group consisting of cholestatic diseases and liver fibrosis. In a particular embodiment, the disease or condition is selected from the group consisting of PBC, PSC, NAFLD, NASH, hepatitis C infection, alcoholic liver disease, liver damage due to progressive fibrosis, liver fibrosis or cirrhosis.

In one embodiment, the disease or condition is PBC. PBC is a chronic disease in which bile ducts in the liver are gradually destroyed. This results in bile accumulating in the liver, contributing to tissue damage and scarring, or fibrosis, that lead to cirrhosis. The PBC can be advanced stage PBC. "Advanced stage PBC" refers to PBC characterized by one or more of the following: Baseline total bilirubin>upper liming of normal (ULN); Baseline total ALP>5×ULN; Baseline transient elastography (TE)>10.7 kPa; Cirrhosis based on an initial or baseline biopsy result or patient having an Ishak score 6 (cirrhosis) or Ludwig/Scheuer PBC Stage 4; or Medical history of ascites, hepatic cirrhosis, jaundice, portal hypertension, portal hypertensive gastropathy or varices esophageal.

In one embodiment, the disease or condition is PSC. PSC is a rare disease that attacks the bile ducts. In PSC, bile ducts become scarred. They slowly narrow until bile backs up into liver and starts to damage it.

NAFLD is a medical condition that is characterized by the buildup of fat (called fatty infiltration) in the liver. NAFLD is one of the most common causes of chronic liver disease and encompasses a spectrum of conditions associated with lipid deposition in hepatocytes. It ranges from steatosis (simple fatty liver), to NASH, to advanced fibrosis and cirrhosis. The disease is mostly silent and is often discovered through incidentally elevated liver enzyme levels. NAFLD is strongly associated with obesity and insulin resistance and is currently considered by many as the hepatic component of the metabolic syndrome.

NASH is a condition that causes inflammation and accumulation of fat and fibrous (scar) tissue in the liver. Liver enzyme levels in the blood may be more elevated than the mild elevations seen with nonalcoholic fatty liver (NAFL). Although similar conditions can occur in people who abuse alcohol, NASH occurs in those who drink little to no alcohol. NASH affects 2 to 5 percent of Americans and is most frequently seen in people with one or more of the following conditions: obesity, diabetes, hyperlipidemia, insulin resistance, uses of certain medications, and exposure to toxins. NASH is an increasingly common cause of chronic liver disease worldwide and is associated with increased liver-related mortality and hepatocellular carcinoma, even in the absence of cirrhosis. NASH progresses to cirrhosis in 15-20% of affected individuals and is now one of the leading indications for liver transplantation in the United States.

Further provided herein are methods of treating cholestatic diseases (such as PBC or PSC), NAFLD, NASH, hepatitis C infection, alcoholic liver disease, liver damage due to progressive fibrosis, liver fibrosis or cirrhosis in a patient in need thereof by administering an effective amount of an oral dosage form described above.

In particular embodiment, the method is a method of treating PBC by administering an effective amount of an oral dosage form described above. In one embodiment, the method is a method of treating PBC by administering an oral dosage form described herein.

In still another embodiment, the method is a method of treating PSC by administering an effective amount of an oral dosage form described above. In one embodiment, the method is a method of treating PSC by administering an oral dosage form described herein.

In another embodiment, the method is a method of treating NAFLD by administering an effective amount of an oral dosage form described above. In one embodiment, the method is a method of treating NAFLD by administering an oral dosage form described herein.

In another embodiment, the method is a method of treating NASH by administering an effective amount of an oral dosage form described above. In one embodiment, the method is a method of treating NASH by administering an oral dosage form described herein. The NASH patient can be a high-risk NASH patient. A "high risk NASH patient" refers to characterization by one or more of: NAS>4; baseline fibrosis stage 2 or 3; or baseline fibrosis stage 1 with a comorbidity (type 2 diabetes, BMI>30 kg/m2 or ALT>60 U/L).

In yet another embodiment, the method is a method of treating fibrosis by administering an effective amount of an oral dosage form described above. In one embodiment, the fibrosis is selected from the group consisting of liver fibrosis, kidney fibrosis, and intestinal fibrosis. In a further embodiment, the fibrosis is liver fibrosis, such as progressive liver fibrosis. In one embodiment, the method is a method of treating fibrosis by administering an oral dosage form described herein. In another embodiment, the present disclosure provides a method for inhibiting or reversing fibrosis, in particular a method for inhibiting or reversing liver fibrosis, comprising administering a therapeutically effective amount of the oral dosage form of the present disclosure to a subject in need thereof. In one embodiment, the subject has liver fibrosis and is not suffering from a cholestatic condition. In another embodiment, the subject is suffering from liver fibrosis and a cholestatic condition.

In one embodiment, the subject has liver fibrosis associated with a disease selected from the group consisting of hepatitis B; hepatitis C; parasitic liver diseases; post-transplant bacterial, viral and fungal infections; alcoholic liver disease; NAFLD; NASH; liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; alpha-1-antitrypsin (al-antitrypsin) deficiency; Zellweger syndrome; tyrosinemia; fructosemia; galactosemia; vascular derangement associated with Budd-Chiari syndrome, veno-occlusive disease, or portal vein thrombosis; and congenital hepatic fibrosis.

In another embodiment, the subject has intestinal fibrosis associated with a disease selected from the group consisting of Crohn's disease, ulcerative colitis, post-radiation colitis, and microscopic colitis.

In another embodiment, the subject has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

In yet another embodiment, the method is a method of treating cirrhosis by administering an effective amount of an oral dosage form described above. In one embodiment, the method is a method of treating cirrhosis by administering an oral dosage form described herein.

In one embodiment, the disease or condition is hyperlipidemia. In one embodiment, the oral dosage form of the present disclosure is useful for treating or preventing NAFLD or NASH that is associated with hyperlipidemia. In one embodiment, the composition of the present disclosure is useful for treating or preventing NASH that is associated with hyperlipidemia.

In another embodiment, the disease or condition is a cardiovascular disease. In another embodiment, the cardiovascular disease is atherosclerosis, hypercholesteremia, or hypertriglyceridemia.

In another aspect, the oral dosage form of the present disclosure is also useful for decreasing liver enzymes. In one embodiment, the subject in need of decreasing liver enzymes is not suffering from a cholestatic condition. In another embodiment, the subject in need of decreasing liver enzymes is suffering from a cholestatic condition. In one embodiment, the liver enzyme is alkaline phosphatase, γ-glutamyl transpeptidase (GGT), and/or 5' nucleotidase.

In certain instances, the methods using the oral dosage form of the invention described herein may also include assessing, monitoring, measuring, or otherwise detecting liver function. Assessing, monitoring, measuring, or otherwise detecting liver function can be performed during the course of any treatment described herein. Liver function can be determined by, for example, assessing, monitoring, measuring, or otherwise detecting a level of one or more liver biomarkers compared to a control. In certain instances, the control is a baseline taken from the patient before beginning treatment. In other instances, the control is preestablished baseline considered as a normal value. Values for measure or detection of liver function biomarkers and controls can be expressed as a comparison to Upper Limit of Normal (ULN).

Liver biomarkers can be used to ascertain and quantify the efficacy of the course of treatment with an oral dosage form described herein. In other instances, liver biomarkers described herein can be used to ascertain, quantify liver function during the course of treatment with an elafibranor composition described herein. Liver biomarkers can also be used to predict whether a patient or patient population will be susceptible to treatment with an elafibranor composition described herein. In one embodiment, the liver biomarkers used include assessing, monitoring, measuring or otherwise detecting an amount or level of aspartate transaminase (AST), alanine transaminase (ALT), alkaline phosphatase (ALP), bilirubin, glycine conjugated elafibranor, taurine conjugated elafibranor, a bile acid, a bile acid glycine conjugate, or a bile acid taurine conjugate. For example, the liver biomarker assessed, monitored, measured, or detected can be ALP.

Treatment with an oral dosage form described herein can reduce the levels of ALP and/or bilirubin in a subject in need thereof.

In particular, treatment with an oral dosage form described herein can reduce the levels bilirubin, preferably within normal limits, in a subject in need thereof.

In particular, treatment with an oral dosage form described herein can reduce and/or normalize the levels of ALP in a subject in need thereof.

The reduction of ALP levels can be represented by the fold change over ULN. For example, treatment with an oral dosage form described herein can reduce the ALP level of a patient described herein to less than about 5×ULN; less than about 4×ULN, less than about 3×ULN, less than about 2×ULN, less than about 1.7×ULN, less than about 1.5× ULN, less than about 1.25×ULN, or less than about ULN.

Treatment with an oral dosage form described herein can normalize the levels of ALP in a subject in need thereof.

The normalization of ALP levels can be defined as ALP level less than 1.0×ULN.

In another embodiment, one or more biomarkers can stratify a patient population undergoing or who will undergo treatment with an oral dosage form described herein. For example, a PBC patient can be stratified for the risk of hepatocellular carcinoma (HCC).

Also provided herein are methods to reduce or eliminate rejection failure of a liver transplant by administering an effective amount of an oral dosage form described above. In certain instances, administration of an oral dosage form described herein reduces expression or levels of ALP and/or bilirubin. In one embodiment, administration of an oral dosage form described herein reduces ALP and bilirubin levels, thereby reducing transplant complications or rejection. In another embodiment, administration of an effective amount of an oral dosage form described herein increases posttransplantation survival rate of a liver transplantee.

In another aspect of the disclosure is a method of treating a solid-tumor cancer by administering an effective amount of an oral dosage form as described herein. In one embodiment, the method is a method of treating a solid-tumor cancer by administering an oral dosage form described herein. In another aspect, such methods include treating hepatocellular carcinoma (HCC), colorectal cancer, gastric cancer, liver cancer, breast cancer, renal cancer, or pancreatic cancer by administering an oral dosage form as described herein. In one embodiment is a method of treating HCC by administering an effective amount of an oral dosage form as described herein. In one embodiment is a method of treating colorectal cancer by administering an effective amount of an oral dosage form as described herein. In another embodiment is a method of treating gastric cancer by administering an effective amount of an oral dosage form as described herein. In another embodiment is a method of treating liver cancer by administering an effective amount of an oral dosage form as described herein. In still another embodiment is a method of treating renal cancer by administering an effective amount of an oral dosage form as described herein. In still another embodiment is a method of treating pancreatic cancer by administering an effective amount of an oral dosage form as described herein. It is understood that the treatment of a cancer described herein can also be performed by administering an effective amount of an oral dosage form described herein in combination with one or more anticancer agents.

In one embodiment, the subject is suffering from a cholestatic condition associated with a disease or condition selected from the group consisting of cancers, such as, e.g., cancers as described herein, including primary liver and biliary cancer, metastatic cancer, sepsis, chronic total parenteral nutrition, cystic fibrosis, and granulomatous liver disease.

In one embodiment, a cholestatic condition is defined as having an abnormally elevated serum level of alkaline phosphatase, γ-glutamyl transpeptidase (GGT), and/or 5' nucleotidase. In another embodiment, a cholestatic condition is further defined as presenting with at least one clinical symptom. In one embodiment, the symptom is itching (pruritus). In another embodiment, a cholestatic condition is selected from the group consisting of primary biliary cholangitis (PBC), primary biliary cirrhosis, primary sclerosing cholangitis (PSC), biliary atresia, drug-induced cholestasis, cholestasis, intrahepatic cholestasis of pregnancy, progressive familial intrahepatic cholestasis (PFIC), infectious cholangitis, cholangitis associated with Langerhans cell histiocytosis, Alagille syndrome, nonsyndromic ductal paucity, and total parenteral nutrition-associated cholestasis. In a preferred embodiment, the cholestatic disease is PBC or PSC.

In another aspect, the present disclosure also provides a method for treating or preventing all forms of conditions related to elevated lipid levels. In one embodiment, the condition is hyperlipidemia where it is associated with a condition selected from resistant primary biliary cholangitis; primary biliary cholangitis where there is associated liver function test elevation and hyperlipidemia, primary sclerosing cholangitis, non-alcohol-induced steatohepatitis; resistant primary biliary cirrhosis; primary biliary cirrhosis where there is associated liver function test elevation and hyperlipidemia, primary sclerosing cholangitis, non-alcohol-induced steatohepatitis; and chronic liver disease associated with hepatitis B, hepatitis C or alcohol consumption. In another embodiment, the present disclosure provides a method for treating or preventing hyperlipidemia, where the hyperlipidemia is primary hyperlipidemia with or without a genetic component, or hyperlipidemia associated with coronary artery disease, cerebrovascular arterial disease, peripheral vascular disease, aortic aneurisms, or carotid atherosclerosis.

In one aspect, the present disclosure provides a method for treating or preventing primary sclerosing cholangitis, as well as chronic hepatitis caused by hepatitis B, hepatitis C or by alcohol. In one aspect, the present disclosure provides a method for treating or preventing other arterial disorders associated with hyperlipidemia. In one aspect, the present disclosure provides a method for treating or preventing hypertriglyceridemia.

One of the advantages of the oral solid dosage forms of the present disclosure includes a decrease in the incidence and/or severity of pruritus in subjects treated with the oral solid dosage forms and according to the methods of the present disclosure. In one embodiment, the incidence of pruritus decreases by at least 5%, 10%, 15%, 20%, 25%, 30%, 35%, 40%, 45%, or 50% in subjects treated with the compositions of the present disclosure.

Elafibranor oral dosage forms described herein can be administered in accordance with a dosing regimen. A dosing regimen refers to continual and intermittent administration of an oral dosage form described herein at one or more of the amounts described herein. Thus, in certain instances, a dosing regimen can include administration of an oral dosage form described herein continually for any number of days, weeks, months, or years as set forth herein. In other instances, a dosing regimen can include administration of an oral dosage form described herein intermittently, where, for example, the composition is administered for one period of time followed by a rest period or off period where the oral dosage form is not administered.

Dosing regimen of the oral dosage form described herein include administration of such oral dosage form daily (QD), every other day (Q2D), once a week (QW), twice a week (BID), three times a week (TIW), once a month (QM), or twice a month (Q2M). In one embodiment, an oral dosage form described herein is administered QD. Thus, an effective amount of an elafibranor composition described herein can be administered QD to treat a disease or condition described herein.

In another embodiment, an oral dosage form described herein is administered Q2D. An effective amount of an oral dosage form described herein can be administered Q2D to treat a disease or condition described herein. In another embodiment, an oral dosage form as described herein is administered QW. An effective amount of an oral dosage form described herein can be administered QW to treat a disease or condition described herein.

In another embodiment, an oral dosage form is described herein administered BID. An effective amount of an oral dosage form described herein can be administered BID to treat a disease or condition described herein.

In another embodiment, an oral dosage form is described herein administered TIW. An effective amount of oral dosage form composition described herein can be administered TIW to treat a disease or condition described herein.

In another embodiment, an oral dosage form is described herein administered QM. An effective amount of an oral dosage form described herein can be administered QM to treat a disease or condition described herein.

In another embodiment, an oral dosage form is described herein administered Q2M. An effective amount of an oral dosage form described herein can be administered Q2M to treat a disease or condition described herein.

The oral dosage form described herein can be administered for any number of days, weeks, months, or years, including indefinitely, provided that the dosage remains efficacious for the patient and the patient tolerates the dosage (e.g., an adjusted or readjusted dose as described herein). In certain instances, an oral dosage form described herein is administered to a patient described herein until loss of efficacy, or until development of unacceptable toxicity or undesired adverse effects. Daily dosing of an oral dosage form described herein can be dependent upon patient tolerance to the dosage, composition, or frequency of administration.

The amount of an oral dosage form described herein administered to a patient can be determined by the existence of any preexisting conditions in the patient.

Further provided herein is a method of treating PBC in a patient in need thereof by administering an effective amount of an oral dosage form described herein QD, where the effective amount is either a 80 mg or 120 mg dose.

Also provided herein are methods of treating a disease or condition described herein, wherein the treatment further includes administration of one or more other active agent(s). For example, UDCA is commonly administered for treatment of PBC, yet a majority of patients administered UDCA alone have either an inadequate response or no response to the treatment. In such instances, there is a need for new medicaments or additional medicaments for the treatment of PBC. The oral dosage form described herein can be administered as described herein (e.g., according to one or more dosing regimens provided above) in combination with UDCA. In some instances, UDCA is administered at an amount of about 10 to 15 mg/kg/day. In another instance, UDCA is administered at an amount of about 300, 600, 900, or 1200 mg/day. Administration of UDCA can include a rest or off period of 1, 2, 3, or 4 weeks. In one example, an oral dosage form described herein is administered as described herein in combination with UDCA, where the UDCA is administered at an amount provided above or in accordance with a package insert. The term package insert refers to instructions customarily included in commercial packages of medicaments approved by the FDA or a similar regulatory agency of a country other than the USA, which contains information about, for example, the usage, dosage, administration, contraindications, and/or warnings concerning the use of such medicaments.

In another example, the other active agent is a peroxisome proliferator-activated receptor alpha (PPARa) agonist, a peroxisome proliferator-activated receptor delta (PPARd) agonist, a dual PPARa/d agonist, a dual PPARa/g agonist, or pan-PPAR agonist, an HMG CoA reductase inhibitor, a GLP1 agonist, insulin, insulin mimetic, metformin, a GTP4 agonist, an HST2 inhibitor, a DPP-IV inhibitor, an SGLT2 inhibitor or a hydroxysteroid dehydrogenase (HSD) inhibitor, such as an 11 β-HSD1 inhibitor, an ASK1 inhibitor, an ACC1 inhibitor, a NOX1 and/or NOX4 inhibitor, or an inhibitor or antagonist of one or more chemokine receptors, such as, for example, CCR2 and CCR5.

In instances where an oral dosage form described herein is useful for the treatment of a cancer described herein, such compositions can be co-administered with one or more anticancer agent(s).

The disclosure is further illustrated by the following examples. It is to be understood that the examples are provided to illustrate certain embodiments and that no limitation to the scope of the disclosure is intended.

EXAMPLES

Example 1: Particle Size Analysis

Particle size of agglomeration was identified as playing a primary role in the dissolution and variability in the blend uniformity and content uniformity of tablet formulations. In order to obtain suitable particle size distribution, milling of elafibranor was investigated. The micronisation process acts to accelerate grains of powder, with an air jet, in a tornado like flow path within the micronisation chamber of the mill. As particles travel in the circular path, they collide, which leads to a reduction in particle size. Centrifugal force directs larger particles to the outside of the chamber and smaller particles are concentrated in the centre of the mill where they can be transferred to the outlet when the appropriate particle size has been reached.

The micronisation process of elafibranor has been performed with the following jet-mill equipment: Microniser Alpine 200 Aeroplex in ambient conditions of temperature and hygrometry.

The feeder delivers the dosage to the microniser by two screws. This system allows a regularity of the flow. A disposable sleeve is used to separate the air and the micronised product at the end of the microniser.

The micronised elafibranor powder is then collected into polyethylene bags and the obtained weight at the end of the micronisation operation has been recorded.

The criteria obtained were the following:
acceptance criteria: D50%≤5 μm and D90%≤15 μm The values obtained for D50% and D90% and [mean+ standard deviation] calculation obtained are summarized in table 1 below.

TABLE 1

| | Particle size distribution of micronized elafibranor | | | | | | | | |
| | clinical batch | | | | | | | | |
| | (#1) | (#2) | (#3) | (#4) | (#5) | (#6) | (#7) | mean | SD |
| D50% | 2.387 | 3.511 | 2.53 | 4.079 | 2.171 | 2.089 | 2.523 | 2.756 | 0.747 |
| D90% | 6.292 | 10.06 | 6.439 | 10.895 | 6.589 | 6.495 | 6.671 | 7.634 | 1.961 |

Example 2: Improved Manufacturing Process of Elafibranor Tablets

1. Preparation of the Wetting Solution
Purified water is manually weighed into stainless steel vessel.
2. Granulation
2.1 Wet Granulation
Elafibranor, microcrystalline cellulose, povidone and croscarmellose sodium were weighed and directly discharged into the bowl of a mixer. The raw materials were mixed together while the wetting solution was gradually added, until a homogenous wet granulate was obtained.

2.2 Wet Calibration

The wet granulate was directly screened into an air-fluidized bed tank through a rotary screen equipped with a sifter.

2.3 Drying

The tank containing the screened wet granulate was set into an air-fluidized bed drier. Wet granulate was fluidized and dried with air.

2.4 Screening

The dried granulate was directly screened into a stainless-steel container for blending through a rotary screen equipped with a sifter.

3. Final Blending

Croscarmellose sodium, anhydrous colloidal silica and magnesium stearate were weighed and added into the stainless-steel container containing the dried and calibrated granulate.

The mixture was then blended with a bin blender.

4. Tableting

Using a rotary tablet press, the final blend was compressed at a theoretical mass of 450 mg, 300.0 mg, 200.0 mg, 100 mg for elafibranor 180 mg, 120 mg, 80 mg and 40 mg tablets, respectively. Tabletting of elafibranor 40 mg and 120 mg tablets was carried out according to the same process (see amounts and weight in table 4 below).

5. Film Coating 5.1 Film Coating Solution Preparation

Cold water was weighed and charged into the container and Opadry® II was added in small portions under stirring until a homogenous mixture is obtained.

5.2 Coating

Using an automatic coating system, the core tablets were coated at a theoretical mass of 471.0 mg for elafibranor 180 mg, 314.0 mg for elafibranor 120 mg, 220 mg (see table 2) or 209.3 mg (see table 3) for elafibranor 80 mg and 104.7 mg for elafibranor 40 mg coated tablets, respectively.

Example 3: Formula of a Tablet

TABLE 2

Formulation of elafibranor 80 mg tablet (Formulation 1)
Elafibranor tablets

| | Unit Quantity | | |
| | mg/tablet 80 mg strength - Formulation 1 | % w/w | Function |
|---|---|---|---|
| Active ingredient | | | |
| Elafibranor | 80.0 | 36.4 | Active |
| Internal phase | | | |
| Microcrystalline cellulose | 95.6 | 43.5 | Filler |
| Povidone | 10.0 | 4.5 | Binder |
| Croscarmellose sodium | 8.0 | 3.6 | Disintegrating agent |
| Purified Water | — | — | — |
| External phase | | | |
| Anhydrous colloidal silica | 0.4 | 0.2 | Glidant |

TABLE 2-continued

Formulation of elafibranor 80 mg tablet (Formulation 1)
Elafibranor tablets

| | Unit Quantity | | |
| | mg/tablet 80 mg strength - Formulation 1 | % w/w | Function |
|---|---|---|---|
| Croscarmellose sodium | 4.0 | 1.8 | Disintegrating agent |
| Magnesium | 2.0 | 0.9 | Lubricant |
| Coating | | | |
| Opadry® II (white or orange) | 20.0 | 9.1 | Coating agent |
| Purified Water | — | — | — |
| Total weight | 220.0 | 100.0 | — |

Formulation 2 containing 120 mg of elafibranor was obtained from Formulation 1 by multiplying the amounts of each active ingredient and excipient by 1.5.

TABLE 3

Formulations of elafibranor 120 mg tablet (Formulation 3) and
elafibranor 80 mg tablet (Formulation 4)
Elafibranor tablets

| | Unit Quantity | | | |
| | mg/tablet | | | |
| | 120 mg strength Formulation 3 | 80 mg strength Formulation 4 | % w/w | Function |
|---|---|---|---|---|
| Active ingredient | | | | |
| Elafibranor | 120.0 | 80.0 | 38.217 | Active |
| Internal phase | | | | |
| Microcrystalline cellulose | 143.4 | 95.6 | 45.669 | Filler |
| Povidone | 15.0 | 10.0 | 4.777 | Binder |
| Croscarmellose sodium | 12.0 | 8.0 | 3.822 | Disintegrating agent |
| Purified Water | — | — | — | — |
| External phase | | | | |
| Anhydrous colloidal silica | 0.6 | 0.4 | 0.191 | Glidant |
| Croscarmellose sodium | 6.0 | 4.0 | 1.911 | Disintegrating agent |
| Magnesium stearate | 3.0 | 2.0 | 0.955 | Lubricant |
| Coating | | | | |
| Opadry® II (white or orange) | 14.0 | 9.3 | 4.459 | Coating agent |
| Purified Water | — | — | — | — |
| Total weight | 314.0 | 209.3 | 100.0 | — |

TABLE 4

Formulations of elafibranor 180 mg tablet (Formulation 5) and
elafibranor 40 mg tablet (Formulation 6)
Elafibranor tablets

| | Unit Quantity | | | |
| | mg/tablet | | | |
| | 180 mg strength Formulation 5 | 40 mg strength Formulation 6 | % w/w | Function |
| --- | --- | --- | --- | --- |
| Active ingredient | | | | |
| Elafibranor | 180.0 | 40.0 | 38.217 | Active |
| Internal phase | | | | |
| Microcrystalline cellulose | 215.1 | 47.8 | 45.669 | Filler |
| Povidone | 22.5 | 5.0 | 4.777 | Binder |
| Croscarmellose sodium | 18.0 | 4.0 | 3.822 | Disintegrating agent |
| Purified Water | — | — | — | — |
| External phase | | | | |
| Anhydrous colloidal silica | 0.9 | 0.2 | 0.191 | Glidant |
| Croscarmellose sodium | 9.0 | 2.0 | 1.911 | Disintegrating agent |
| Magnesium stearate | 4.5 | 1.0 | 0.955 | Lubricant |
| Coating | | | | |
| Opadry ® II | 21.0 | 4.7 | 4.459 | Coating agent |
| Purified Water | — | — | — | — |
| Total weight | 471.0 | 104.7 | 100.0 | — |

Example 4. Dissolution Testing of Elafibranor Tablets

Before tableting, elafibranor was jet-milled as described above to reduce the particle size of the material. Jet-milling (i.e., micronization) resulted in material that had a smaller, more uniform particle size and increased surface area, leading to faster drug release from tablets containing jet-milled elafibranor.

80 mg and 120 mg elafibranor tablets (Formulations 1 and 2 of Example 3) were observed to assess the release of the drug.

Upon testing, the coated tablets containing elafibranor released at least 75% of the drug within 15 minutes in the conditions of the European Pharmacopeia 5.0 paragraph 2.9.3 Dissolution test for solid dosage forms, using a paddle apparatus.

The method for dissolution used a paddle apparatus (apparatus 2) as described in the general chapter of European Pharmacopeia 2.9.3 and US Pharmacopeia <711> with a dissolution medium of 1000 mL of sodium lauryl sulphate (SLS) at 1.0% and 0.8% in purified water for elafibranor 120 mg and elafibranor 80 mg coated tablets respectively, and a paddle speed of 75 rpm. The conditions were developed by varying the concentration of SLS to obtain sink conditions for the dissolution medium. The defined conditions allowed to discriminate the formulations tested during formulation and process development regarding their dissolution profile. The assay was carried out by liquid chromatography as described in the general chapter of European Pharmacopeia 2.2.29 and US Pharmacopeia <621>; the assay is based on a reversed phase isocratic HPLC with UV detection at 357 nm.

The dissolution release rate of tablets containing jet-milled elafibranor is shown in FIG. 1 (80 mg—Formulation 1) and FIG. 2 (120 mg—Formulation 2).

Example 5: Active Ingredient Content and Uniformity Testing of Elafibranor Tablets Identification and Assay of Elafibranor The analytical method for identification and assay used liquid chromatography as described in the general chapter of European Pharmacopeia 2.2.29 and US Pharmacopeia <621>; it is based on a reversed phase gradient HPLC with UV detection at 350 nm and with PDA detection (wavelength from 200 to 500 nm) for identification. It used a Phenomenex, Synergi Polar-RP column (4 μm particle size, 150×4.6 mm) equilibrated at 25° C. and, as a mobile phase, a binary system of methanol (supplemented with trifluoroacetic acid 0.01%) and water (supplemented with trifluoroacetic acid 0.05%). Tablets were taken up in water and elafibranor was extracted with methanol and injected onto the HPLC column for analysis. The quantitation of elafibranor was carried out using an external standard.

Identifications were performed by retention time (HPLC-UV) and by UV-spectrum (HPLC-PDA) of the active ingredient.

Uniformity of Content

The content uniformity method was performed as described in European Pharmacopeia 2.9.40 and US Pharmacopeia <905>, with the same chromatographic conditions by HPLC as those used for the assay.

The results are shown in FIG. 1 (80 mg—Formulation 1) and FIG. 2 (120 mg—Formulation 2).

Example 7: Stability Studies of 80 mg and 120 mg Elafibranor Tablets

The stability of 80 mg and 120 mg tablets (Formulations 1 and 2) were tested in stability studies.

The stability tests were conducted at 25° C. and 60% relative humidity (RH) for up to 36 months. During these months, the mean mass, the mass uniformity, the disintegration time and the dissolution rate as well as the content of elafibranor and the degradation products have been monitored periodically.

The results for formulation of the 80 mg and 120 mg tablets are shown in FIG. 1 (80 mg—Formulation 1) and FIG. 2 (120 mg—Formulation 2).

Example 8 Drug Used for the Clinical Trial

The stability of 80 mg and 120 mg tablets (Formulations 4 and 3) were tested in stability studies for clinical lots.

The stability tests were conducted at 25° C. and 60% relative humidity (RH) during 60 months for 80 mg dosage and at 30° C. and 75% relative humidity (RH) during 48 months for 120 mg dosage.

During these months, the mean mass, the mass uniformity, the disintegration time and the dissolution time as well as the content of elafibranor and the degradation products have been monitored periodically.

The results for formulation of the 80 mg and 120 mg tablets are shown in FIG. 3 (80 mg—Formulation 4) and FIG. 4 (120 mg—Formulation 3).

Elafibranor was supplied as 80 mg or 120 mg white to offwhite round coated tablets (of different sizes) with no printed inscription. The elafibranor 120 mg and 80 mg tablets contained elafibranor (active ingredient) and excipients (microcrystalline cellulose, povidone, croscarmellose, anhydrous colloidal silica, magnesium stearate, Opadry® II white).

Two placebo tablets (each one of the same size as the corresponding active tablet) to match elafibranor 80 mg or 120 mg were provided as a white to off-white round coated tablet with no printed inscription. The placebo tablets contained the same excipients as the active formulation as well as lactose monohydrate (which was used in place of the active ingredient [elafibranor]).

Beneficial effects of elafibranor on liver function, relevant to PBC, were consistently observed in all Phase 2a clinical studies of subjects treated with 80 mg/day elafibranor for 1 to 3 months and in the Phase 2b clinical trial of subjects treated with 80 mg/day and 120 mg/day elafibranor for 12 months.

Example 9: Phase 2 Clinical Trial

This example describes a double-blind, randomized, placebo-controlled trial to evaluate the efficacy and safety of elafibranor 80 mg and 120 mg once daily (qd) versus placebo in a PBC population.

The study included a screening visit, followed by 12 weeks of double-blind treatment period. Patients attended study visits at randomization, Week 2, 4, 8, 12 during the treatment period.

Elafibranor was administered per os, once daily at 80 mg or 120 mg, for 12 weeks, in the form of tablets of the invention (Formulations 4 and 3). The elafibranor 120 mg and 80 mg tablets contained elafibranor (active ingredient) and excipients (microcrystalline cellulose, povidone, croscarmellose, anhydrous colloidal silica, magnesium stearate, Opadry® II white). The white tablets were provided to the participants in aluminum blisters.

The primary objectives were to compare the effect of daily oral administration of elafibranor 80 mg and 120 mg on changes in serum alkaline phosphatase (ALP) to that of placebo in patients with PBC and inadequate response to Ursodeoxycholic acid (UDCA).

ALP Levels

The primary endpoint of the study was to evaluate the efficacy of elafibranor 80 mg or 120 mg with respect to relative change from baseline in serum ALP levels compared to placebo.

Absolute changes in serum ALP levels were monitored from Baseline to week 2, 4, 8 and 12.

In this study, all subjects had a baseline ALP>1.67×ULN (104 U/L for women) with mean baseline ALP values 2.5 to 3.4×ULN. Baseline GGT values, ranging from 4.5 to 7.8 ULN (36 U/L in women), were also elevated in all treatment arms. Alkaline phosphatase and GGT mean values were slightly lower in the elafibranor 120 mg treatment group and slightly higher in the elafibranor 80 mg treatment group compared to the placebo treatment group.

In the primary efficacy analysis conducted using a non-parametric randomization-based ANCOVA with baseline ALP as covariate, each dose demonstrated a statistically significant treatment effect vs placebo (p<0.001). The treatment effect estimate was −52.0% (95% CI [−62.5; −41.5]) for the elafibranor 80 mg treatment group and −43.9% (95% CI [−55.7; −32.1]) for the elafibranor 120 mg treatment group.

The mean relative change (%) from baseline to endpoint in serum ALP was −48.3% for the elafibranor 80 mg treatment group, −40.6% for the elafibranor 120 mg treatment group, and 3.2% for placebo.

The primary efficacy supportive analysis conducted using an ANCOVA with baseline ALP as a covariate was consistent with the primary efficacy analysis. The treatment effect estimate was −51.4% (95% CI [−63.3; −39.5]) for the elafibranor 80 mg treatment group and −43.9% (95% CI [−55.8; −31.9]) for the elafibranor 120 mg treatment group.

The mean (95% CI) ALP values from baseline through Week 12 are shown in FIG. 5 by treatment group. Both the elafibranor 80 mg and 120 mg treatment groups demonstrated declining mean ALP values over the 12 week study.

Figure 6:
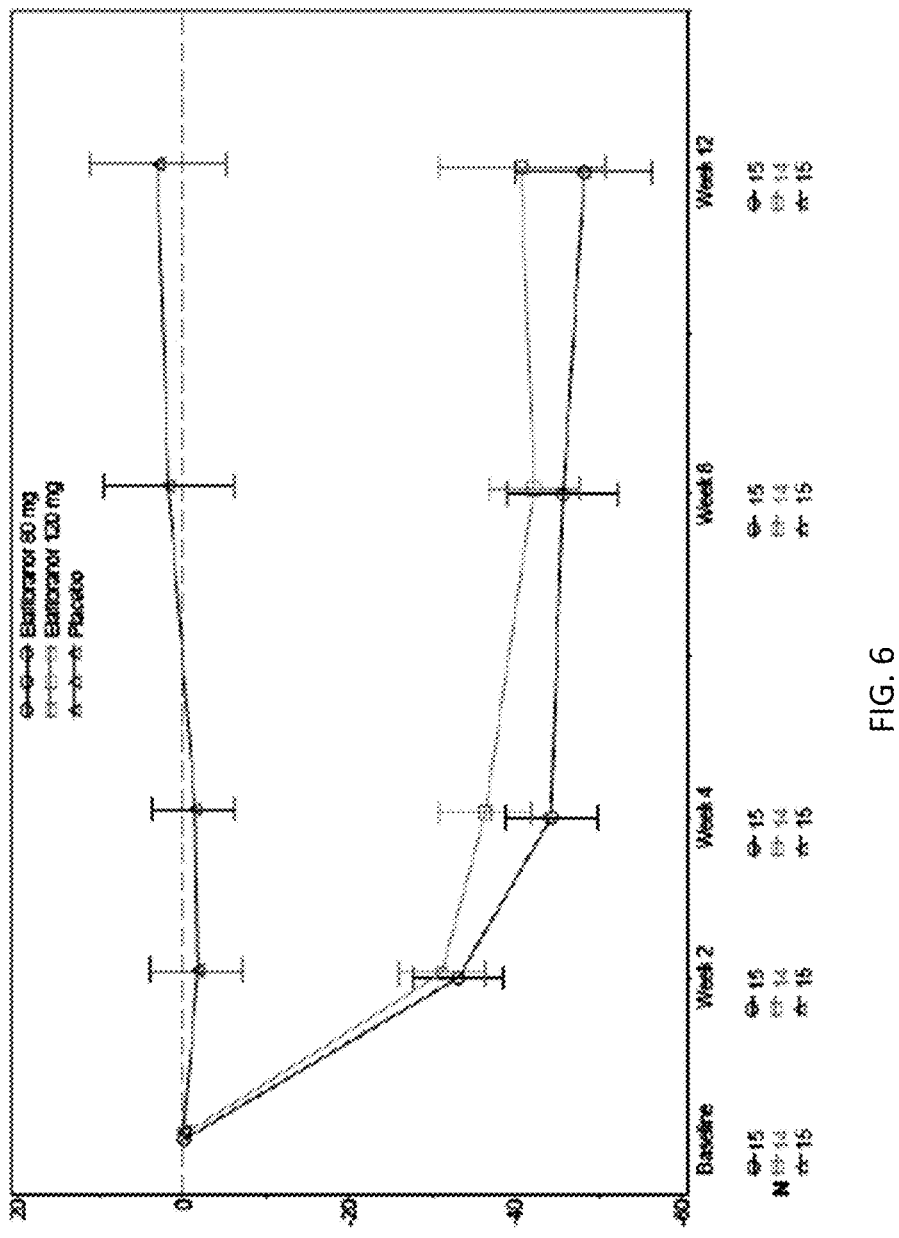
FIG. 6 is a graph showing the mean relative change from baseline through week 12 in ALP in groups of patients treated with an oral solid dosage form according to the invention, comprising either 80 mg or 120 mg of elafibranor (Formulations 4 and 3).

The mean (95% CI) relative changes (%) in ALP values from baseline through Week 12 are shown in FIG. 6 by treatment group. The mean relative changes (%) from baseline shows a decrease in ALP values over time for the elafibranor 80 mg and 120 mg treatment groups beginning at Week 2 and continuing up through Week 12.

The response rates to treatment as defined by at least 10%, 20%, and 40% decrease in ALP from baseline to endpoint analyzed using a Fishers exact test on the mITT set show that both the elafibranor 80 mg and 120 mg treatment groups had a statistically significantly greater proportion of responders in all 3 response categories at endpoint compared to placebo (p<0.001) (FIG. 7).

Response According to Paris I, Paris II, Toronto I and Toronto II Risk Scores

The percentage of patients was calculated who met the definition of PBC responder criteria applying the Paris I, Toronto I, Toronto II, Toronto III, Toronto IV, Mayo II, and Barcelona disease prognostic risk criteria. Paris I risk scores were defined as ALP≤3×ULN and AST≤2×ULN and bilirubin within normal limits.

The response rates to treatment from baseline to endpoint as defined by Paris I risk scores were 80.0%, 78.6%, and 53.3% in the elafibranor 80 mg, elafibranor 120 mg, and placebo groups, respectively.

Paris II risk scores were defined as ALP≤1.5×ULN and AST≤1.5×ULN and bilirubin within normal limits. The response rates to treatment from baseline to endpoint as defined by Paris II risk scores were 53.3%, 50.0%, and 0% in the elafibranor 80 mg, elafibranor 120 mg, and placebo groups, respectively; the proportion of responders was significantly higher in both elafibranor treatment groups compared to placebo (p=0.002 and p=0.002 for GENFIT, GFT505B-216-1 Clinical Study Report: Final v1.0, 14 Jun. 2019 Page 94 of 1663 elafibranor 80 mg vs placebo and elafibranor 120 mg vs placebo, respectively).

Toronto I risk scores were defined as ALP≤1.67×ULN. The response rates to treatment from baseline to endpoint as defined by Toronto I risk scores were 66.7%, 78.6%, and 6.7% in the elafibranor 80 mg, elafibranor 120 mg, and placebo groups, respectively; the proportion of responders was significantly higher in both elafibranor treatment groups compared to placebo (p=0.002 and p<0.001 for elafibranor 80 mg vs placebo and elafibranor 120 mg vs placebo, respectively).

Toronto II risk scores were defined as ALP≤1.75×ULN. The response rates to treatment from baseline to endpoint as defined by Toronto II risk scores were 66.7%, 78.6%, and 6.7% in the elafibranor 80 mg, elafibranor 120 mg, and placebo groups, respectively; the proportion of responders was significantly higher in both elafibranor treatment groups compared to placebo (p=0.002 and p<0.001 for elafibranor 80 mg vs placebo and elafibranor 120 mg vs placebo, respectively).

GGT Levels

The absolute and relative changes from baseline to endpoint in GGT are presented for the mITT set in FIG. 8.

The mean relative change (%) from baseline to endpoint in GGT was −37.1% for the elafibranor 80 mg treatment group, −40.0% for the elafibranor 120 mg treatment group, and 0.2% for placebo.

In the analysis conducted using a non-parametric randomization-based ANCOVA with baseline GGT as covariate on the mITT set, each dose demonstrated a statistically significant treatment effect vs placebo (p≤0.002).

The treatment effect estimate was −38.6% (95% CI [−56.8; −20.4]) for the elafibranor 80 mg treatment group and −39.9% (95% CI [−58.1; −21.6]) for the elafibranor 120 mg treatment group.

Figure 9:
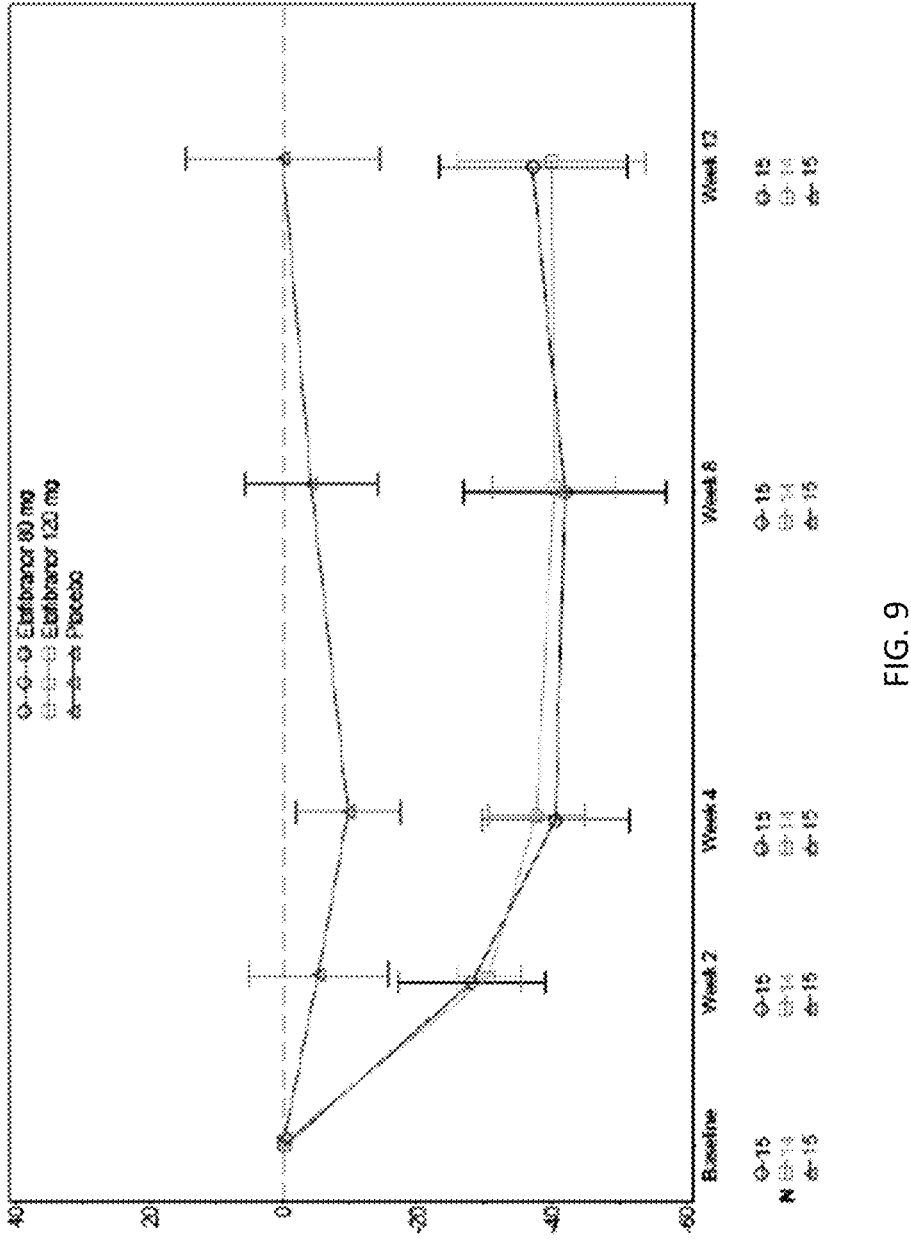
FIG. 9 is a graph showing mean relative change from baseline through week 12 in γ-glutamyl transpeptidase (GGT) by treatment Group (mITT Set).

The mean (95% CI) relative changes (%) in GGT values from baseline through Week 12 are shown in FIG. 9 by treatment group for the mITT set. The mean relative changes (%) from baseline shows a measurable decrease in GGT values as early as Week 2 or the elafibranor 80 mg and 120 mg treatment groups.

Change in Pruritus

Considering that pruritus is a preeminent adverse event in subjects with PBC, assessment of pruritus was also considered. More specifically, the change from baseline in pruritus (through 5D-itch scale (measuring the degree, duration, direction [improvement or worsening], disability [effect on daily activities], and distribution of itching) and visual analogue scale for pruritus (VAS).

The 5D-itch scale is a reliable, multidimensional measure of itching that has been validated in patients with chronic pruritus to detect changes over time (Elman S, et al., The 5-D itch scale: a new measure of pruritus. Br J Dermatol. 2010; 162(3):587-593). The VAS is a reliable and validated method of pruritus assessment (Reich A, et al., Visual analogue scale: evaluation of the instrument for the assessment of pruritus. Acta Derm Venereol. 2012; 92(5):497-501).

Pruritus scoring values and absolute changes from baseline are provided for each domain of the 5D-itch scale (duration, degree, direction, disability, and distribution) and for the VAS by subject and by visit; baseline and endpoint values are flagged in this listing; total scores at each visit are also summarized in this listing.

Summaries of the pruritus scoring values, absolute changes in pruritus scoring values, and relative changes in pruritus scoring values for the 5D-itch scale (duration, degree, direction, disability, and distribution) and for the VAS were assessed. The median relative change from baseline to endpoint in the pruritus VAS were −23.7%, −49.5%, and −7.1% for the elafibranor 80 mg, elafibranor 120 mg, and placebo treatment groups, respectively.

Figure 10:
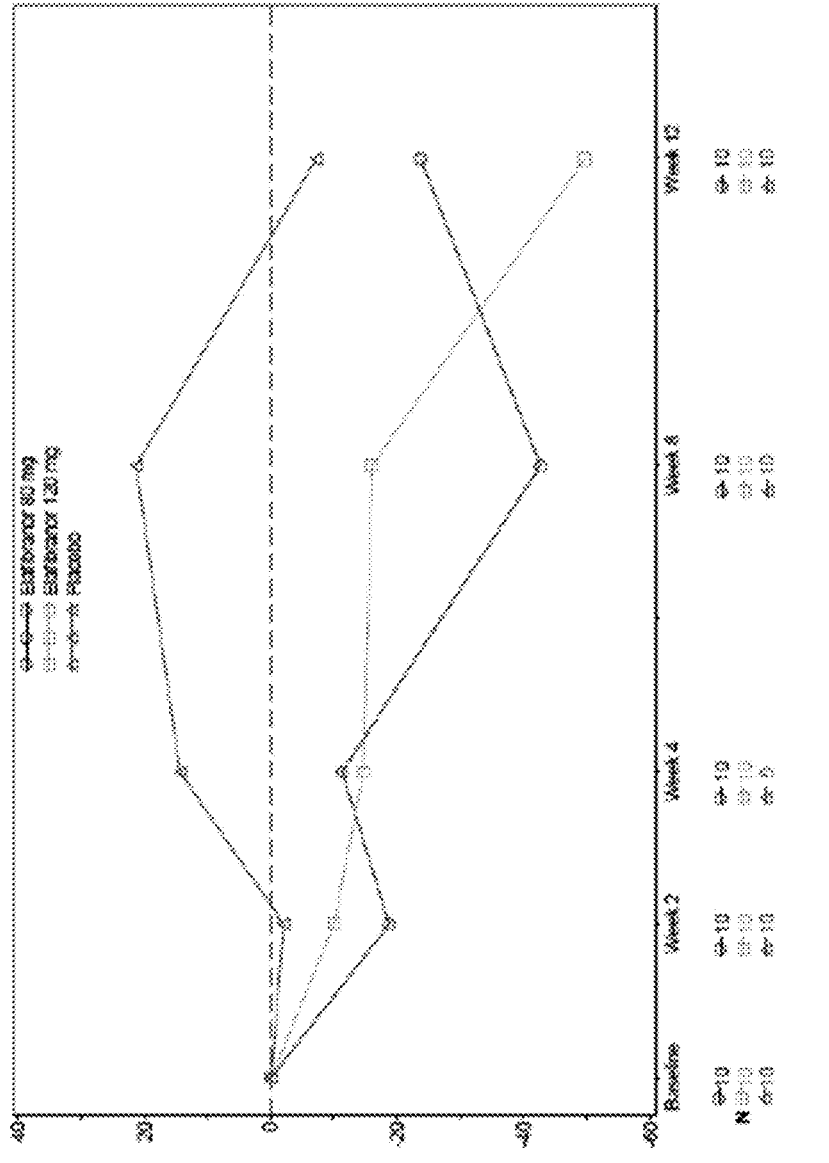
FIG. 10 is a graph showing the median relative change from baseline through week 12 in pruritus visual analogue score (mITT Set).

The median relative changes (%) in the pruritus VAS from baseline through Week 12 are shown in FIG. 10 by treatment group. Both the elafibranor 80 mg and the elafibranor 120 mg treatment groups demonstrated declining median VAS as early as Week 2.

Example 10: Phase 3 Clinical Trial

This example describes a double-blind, randomized, placebo-controlled trial to evaluate the efficacy and safety of elafibranor 80 mg once daily (qd) versus placebo in a PBC population.

The study included a screening visit, followed by 52 weeks of double-blind treatment period. Patients attended study visits at randomization, Week 4, 13, 26, and 39 during the treatment period.

Elafibranor was administered per os, once daily at 80 mg, for 52 weeks, in the form of tablets of the invention (Formulation 4). The elafibranor 80 mg tablets contained elafibranor (active ingredient) and excipients (microcrystalline cellulose, povidone, croscarmellose, anhydrous colloidal silica, magnesium stearate, Opadry® II white). The white tablets were provided to the participants in aluminum blisters.

The primary objectives were to compare the effect of daily oral administration of elafibranor 80 mg on changes in relevant biochemical indicators of cholestasis or in pruritus to that of placebo in patients with PBC with an inadequate response or intolerance to Ursodeoxycholic acid (UDCA).

A biochemical response (the primary end point) was observed in 51% of the patients (55 of 108) who received elafibranor and in 4% (2 of 53) who received placebo, for a difference of 47 percentage points (95% confidence interval [CI], 32 to 57; P<0.001). The alkaline phosphatase level normalized in 15% of the patients in the elafibranor group and in none of the patients in the placebo group at week 52 (difference, 15 percentage points; 95% CI, 6 to 23; P=0.002). Among patients who had moderate-to-severe pruritus (44 patients in the elafibranor group and 22 in the placebo group), the least-squares mean change from baseline through week 52 on the WI-NRS did not differ significantly between the groups (−1.93 vs. −1.15; difference, −0.78; 95% CI, −1.99 to 0.42; P=0.20).

Example 11: Photostability Stress Study

Two lots of 80 mg elafibranor tablets (Formulation 4 of Example 3) were observed to assess the photostability:

Tablets comprising Opadry® Orange (=Opadry® Orange coated tablets=LOT M0002)

Tablets comprising Opadry® White (=Opadry® White coated tablets=LOT M0003)

After exposure to UV light according to ICH guidelines for photostability testing (ICH guideline "*Stability testing: photostability testing of new drugs substances and products Q1*") of naked tablets M0002 and M0003, three test are performed:

Description test: observing any color changes before and after UV exposure;

Elafibranor content test: measurement of elafibranor content before and after UV exposure; and Impurities test: measurement of impurities in the tablets before and after UV exposure.

Composition of Opadry® Coating

Opadry® White=Opadry® 11 complete film coating system 85F18422 White=polyvinyl alcohol, titanium dioxide, polyethylene glycol/macrogol and talc.

Opadry® Orange=Opadry® II complete film coating system 85F53893 ORANGE=polyvinyl alcohol, titanium dioxide, polyethylene glycol/macrogol, talc and FD&C yellow #6/sunset yellow FCF aluminium lake.

List of Materials

| EQUIPMENT/ MATERIALS | MODEL/ACTIVE SUBSTANCE | ID | S/N |
|---|---|---|---|
| HPLC | AGILENT 1260 INFINITY II | LC35 | I |

-continued

| EQUIPMENT/ MATERIALS | MODEL/ACTIVE SUBSTANCE | ID | S/N |
|---|---|---|---|
| COLUMN | PHENOMENEX SINERGY POLAR RP80 A 150 × 4.6 mm 4 μm | I | H18 - 057613 |
| BALANCE (M0002 M0003 M0002 EXPOSED SAMPLES) | METTLER TOLEDO XP205 | BILANCIA 18 | 1128450767 |
| BALANCE (M0003 EXPOSED SAMPLES) | METTLER TOLEDO XPE205 DR | BILANCIA22 | B718060349 |
| GFT505 REFERENCE STANDARD | ELAFIBRANOR batch 19001548MIC | / | / |

Results

Description Results:

LOT M0002 (Opadry® Orange coated): no difference can be noticed between stressed and non-stressed sample. No change in appearance or colour is observed.

LOT M0003 (Opadry® White coated): a significant degradation of the original color is observed. The stressed samples (exposed to UV) turn from white to a light pink coloration.

Elafibranor Content Results:

Table 5 shows that both stressed samples of batches M0002 and M0003 fully meet the specification criteria for test "GFT505 content". It can be noticed a slight decrease of GFT505 content for M0003.

TABLE 5

| Sample | Amount (mg/tab) | exposed tablets content/non-exposed tablet content (%) |
|---|---|---|
| M0002 - non exposed | 79.5 | / |
| M0002 - exposed | 80.1 | 100.8 |
| M0003 - non exposed | 79.2 | / |
| M0003 - exposed | 77.1 | 97.3 |

Impurities Results:

Table 6 shows that stressed samples of batch M0002 fully meet the specification criteria for impurities test. All impurities are found under limit of quantification (LOQ) and under limit of rejection (LOR).

Table 6 also shows the presence of unknown impurities RRT 1.28, RRT 1.32 and RRT1.68 in batch M0003 after UV exposure. This huge increase for unknown impurities is over specification limits.

TABLE 6

| Sample | GFT 1020 | RRT 0.88 | GFT 1459 | GFT 1372 | RRT 1.28 | RRT 1.32 | RRT 1.34 | GFT 690 | RRT1 .64 | RRT 1.68 |
|---|---|---|---|---|---|---|---|---|---|---|
| M0002 non-exposed | / | 0.02 | 0.01 | 0.01 | / | / | 0.02 | 0.01 | / | / |
| M0002 exposed | / | 0.01 | 0.01 | 0.01 | 0.01 | 0.01 | 0.01 | 0.01 | / | 0.04 |
| M0003 non-exposed | / | 0.01 | 0.01 | 0.01 | / | / | 0.02 | 0.02 | / | / |
| M0003 exposed | 0.02 | 0.02 | 0.02 | 0.02 | 0.20 | 0.15 | 0 | 0.02 | 0.01 | 0.18 |

CONCLUSION

The tablets M0002 fully meet specification criteria for photostability test. No issues are risen about Opadry® orange coating. On the other hand, tablets M0003 show a significant increase of unknown impurities and show a light pink coloring after photostability stress test. In conclusion, a coloring agent is needed to obtained photostability of the tablet.

The invention claimed is:

1. An oral solid dosage form in the form of a tablet, comprising:

(a) an internal phase comprising:

i) from 20 to 60% by weight of the tablet, of elafibranor or a pharmaceutically acceptable salt or ester thereof;

ii) a filler selected from the group consisting of mannitol, microcrystalline cellulose, and lactose monohydrate;

iii) a disintegrating agent selected from the group consisting of crospovidone and croscarmellose sodium; and iv) a binder selected from the group consisting of hydroxypropylcellulose, copovidone, povidone, and hydroxypropylmethyl cellulose, and (b) an external phase comprising a disintegrating agent selected from the group consisting of crospovidone and croscarmellose sodium, colloidal silica as a glidant, and magnesium stearate as a lubricant, wherein the external phase (b) is free of elafibranor;

wherein the elafibranor or the pharmaceutically acceptable salt or ester thereof is micronized.

2. An oral solid dosage form in the form of a tablet, comprising:

(a) an internal phase comprising:

i) from 20 to 60% by weight of the tablet, of elafibranor or a pharmaceutically acceptable salt or ester thereof;

ii) a filler selected from the group consisting of mannitol, microcrystalline cellulose, and lactose monohydrate;

iii) a disintegrating agent selected from the group consisting of crospovidone and croscarmellose sodium; and iv) a binder selected from the group consisting of hydroxypropylcellulose, copovidone, povidone, and hydroxypropylmethyl cellulose, and (b) an external phase comprising a disintegrating agent selected from the group consisting of crospovidone and croscarmellose sodium, colloidal silica as a glidant, and magnesium stearate as a lubricant, wherein the external phase (b) is free of elafibranor;

wherein the elafibranor or the pharmaceutically acceptable salt or ester thereof is in the form of particles, and wherein at least 90% of the particles have a diameter of 15 μm or less.

3. The oral solid dosage form according to claim 2, wherein at least 50% of the particles have a diameter of 5 μm or less.

4. The oral solid dosage form according to claim 1, wherein the dosage form comprises from 35 to 40% by weight of the elafibranor or the pharmaceutically acceptable salt or ester thereof.

5. The oral solid dosage form according to claim 1, wherein the dosage form comprises from 35 mg to 180 mg of the elafibranor or the pharmaceutically acceptable salt or ester thereof.

6. The oral solid dosage form according to claim 5, wherein the dosage form comprises from 40 mg to 120 mg of the elafibranor or the pharmaceutically acceptable salt or ester thereof.

7. The oral solid dosage form according to claim 1, wherein
(a) the internal phase comprises:
   (i) from 30% to 60% by weight of the elafibranor or the pharmaceutically acceptable salt or ester thereof;
   (ii) from 20% to 55% by weight of microcrystalline cellulose;
   (iii) from 0.8% to 6% by weight of croscarmellose sodium; and
   (iv) from 2% to 6% by weight of povidone; and
(b) the external phase comprises:
   from 0.2% to 4% by weight of croscarmellose sodium;
   from 0.1% to 0.4% by weight of colloidal silica; and
   from 0.1% to 2% by weight of magnesium stearate;
   relative to the total weight of the tablet.

8. The oral solid dosage form according to claim 1, wherein the tablet is obtained by carrying out a step of wet granulation followed by tablet compression and optionally, coating.

9. The oral solid dosage form according to claim 1, said dosage form comprising an external coating.

10. The oral solid dosage form according to claim 9, wherein the external coating comprises a coloring agent.

11. A method for treating or preventing primary biliary cholangitis (PBC), primary sclerosing cholangitis (PSC), nonalcoholic fatty liver disease (NAFLD), nonalcoholic steatohepatitis (NASH), cirrhosis, hepatitis C infection, alcoholic liver disease, liver damage due to progressive fibrosis, liver fibrosis or cirrhosis in a patient in need thereof, the method comprising administering the oral solid dosage form according to claim 1.

12. The method according to claim 11, wherein said oral solid dosage form is administered once a day.

13. The oral solid dosage form according to claim 1, wherein the elafibranor or the pharmaceutically acceptable salt or ester thereof is the sole active ingredient.

14. The oral solid dosage form according to claim 1, consisting of:
(a) the internal phase consisting of:
   i) from 20 to 60% by weight of the elafibranor or the pharmaceutically acceptable salt or ester thereof;
   ii) the filler selected from the group consisting of mannitol, microcrystalline cellulose, and lactose monohydrate;
   iii) the disintegrating agent selected from the group consisting of crospovidone and croscarmellose sodium; and
   iv) the binder selected from the group consisting of hydroxypropylcellulose, copovidone, povidone, and hydroxypropylmethyl cellulose, and
(b) the external phase consisting of the disintegrating agent selected from the group consisting of crospovidone and croscarmellose sodium, colloidal silica as the glidant, and magnesium stearate as the lubricant,
wherein the external phase (b) is free of elafibranor.

15. The oral solid dosage form according to claim 1, consisting of:
(a) the internal phase consisting of:
   i) from 20 to 60% by weight of the tablet of the elafibranor or the pharmaceutically acceptable salt or ester thereof;
   ii) the filler selected from the group consisting of mannitol, microcrystalline cellulose, and lactose monohydrate;
   iii) the disintegrating agent selected from the group consisting of crospovidone and croscarmellose sodium; and
   iv) the binder selected from the group consisting of hydroxypropylcellulose, copovidone, povidone, and hydroxypropylmethyl cellulose,
(b) the external phase consisting of the disintegrating agent selected from the group consisting of crospovidone and croscarmellose sodium, colloidal silica as the glidant and magnesium stearate as the lubricant, and
(c) an external coating,
wherein the external phase (b) and the external coating (c) are free of elafibranor.

* * * * *